(12) United States Patent
Castleberry et al.

(10) Patent No.: US 10,201,351 B2
(45) Date of Patent: Feb. 12, 2019

(54) CONTINUOUS EMBOLIC COIL AND METHODS AND DEVICES FOR DELIVERY OF THE SAME

(71) Applicant: ENDOSHAPE, INC., Boulder, CO (US)

(72) Inventors: Jeffrey Castleberry, Longmont, CO (US); William Aldrich, Napa, CA (US); Charles Barkenbus, Longmont, CO (US); Stan Needle, Louisville, CO (US)

(73) Assignee: Endoshape, Inc., Boulder, CO (US)

( * ) Notice: Subject to any disclaimer, the term of this patent is extended or adjusted under 35 U.S.C. 154(b) by 56 days.

(21) Appl. No.: 14/775,590

(22) PCT Filed: Mar. 13, 2014

(86) PCT No.: PCT/US2014/026315
§ 371 (c)(1),
(2) Date: Sep. 11, 2015

(87) PCT Pub. No.: WO2014/160320
PCT Pub. Date: Oct. 2, 2014

(65) Prior Publication Data
US 2016/0022274 A1    Jan. 28, 2016

Related U.S. Application Data

(60) Provisional application No. 61/779,360, filed on Mar. 13, 2013.

(51) Int. Cl.
*A61B 17/12* (2006.01)
*A61B 17/00* (2006.01)
*A61B 90/00* (2016.01)

(52) U.S. Cl.
CPC .. *A61B 17/12145* (2013.01); *A61B 17/12031* (2013.01); *A61B 17/12109* (2013.01);
(Continued)

(58) Field of Classification Search
CPC ........ A61B 17/12145; A61B 17/12031; A61B 17/12109; A61B 17/2113; A61B 17/12118; A61B 17/3966; A61B 17/12022; A61B 17/1214–17/12154; A61B 17/00367; A61B 2017/0053; A61B 2017/00867; A61B 2017/00871; A61B 2017/12054; A61B 2017/1205; A61B 17/0467; A61B 2017/320766; A61F 2/01; A61F 2/013; A61F 2002/011; A61M 2025/004
USPC ....................................................... 606/200
See application file for complete search history.

(56) References Cited

U.S. PATENT DOCUMENTS

| 4,503,569 A | 3/1985 | Dotter |
| 4,606,336 A | 8/1986 | Zeluff |

(Continued)

FOREIGN PATENT DOCUMENTS

| CA | 2527976 A1 | 12/2004 |
| EP | 2098174 A2 | 9/2009 |

(Continued)

OTHER PUBLICATIONS

PCT International Search Report and Written Opinion dated Nov. 11, 2014, PCT Application No. PCT/US2014/026315, 13 pages.

(Continued)

*Primary Examiner* — Ryan J Severson
*Assistant Examiner* — Charles Wei
(74) *Attorney, Agent, or Firm* — Dorsey & Whitney LLP

(57) ABSTRACT

An occlusion system (5) provides a trimmable continuous embolic coil (10) that is "cut to length" at the end of its deployment into the target occlusion site. A delivery device (15) provides the "cut to length" feature for the continuous embolic coil.

6 Claims, 13 Drawing Sheets

(52) U.S. Cl.
CPC .. *A61B 17/12113* (2013.01); *A61B 17/12118* (2013.01); *A61B 2017/0053* (2013.01); *A61B 2017/00367* (2013.01); *A61B 2017/00867* (2013.01); *A61B 2017/00871* (2013.01); *A61B 2017/12054* (2013.01); *A61B 2090/3966* (2016.02)

(56) References Cited

U.S. PATENT DOCUMENTS

| | | | |
|---|---|---|---|
| 4,950,258 | A | 8/1990 | Kawai et al. |
| 4,994,069 | A | 2/1991 | Ritchart et al. |
| 5,163,952 | A | 11/1992 | Froix |
| 5,258,020 | A | 11/1993 | Froix |
| 5,599,291 | A | 2/1997 | Balbierz et al. |
| 5,603,722 | A | 2/1997 | Phan et al. |
| 5,649,949 | A | 7/1997 | Wallace et al. |
| 5,674,242 | A | 10/1997 | Phan et al. |
| 5,800,455 | A | 9/1998 | Palermo et al. |
| 5,830,230 | A | 11/1998 | Berryman et al. |
| 5,941,888 | A | 8/1999 | Wallace et al. |
| 5,964,744 | A | 10/1999 | Balbierz |
| 6,086,577 | A | 7/2000 | Ken et al. |
| 6,090,063 | A * | 7/2000 | Makower ......... A61B 17/12022 604/13 |
| 6,090,125 | A | 7/2000 | Horton |
| 6,160,084 | A | 12/2000 | Langer et al. |
| 6,165,198 | A | 12/2000 | McGurk et al. |
| 6,221,066 | B1 | 4/2001 | Ferrera et al. |
| 6,248,129 | B1 | 6/2001 | Froix |
| 6,281,262 | B1 | 8/2001 | Shikinami |
| 6,312,421 | B1 * | 11/2001 | Boock ............ A61B 17/12022 604/509 |
| 6,368,356 | B1 | 4/2002 | Zhong et al. |
| 6,383,204 | B1 | 5/2002 | Ferrera |
| 6,388,043 | B1 | 5/2002 | Langer et al. |
| 6,458,137 | B1 * | 10/2002 | Klint ............ A61B 17/12022 606/108 |
| 6,550,480 | B2 | 4/2003 | Feldman et al. |
| 6,551,305 | B2 | 4/2003 | Ferrera et al. |
| 6,554,849 | B1 | 4/2003 | Jones et al. |
| 6,616,617 | B1 | 9/2003 | Ferrera et al. |
| 6,712,810 | B2 | 3/2004 | Harrington et al. |
| 6,720,402 | B2 | 4/2004 | Langer et al. |
| 6,730,119 | B1 | 5/2004 | Smalling |
| 6,740,094 | B2 | 5/2004 | Maitland et al. |
| 6,746,461 | B2 | 6/2004 | Fry |
| 6,763,833 | B1 * | 7/2004 | Khera .................. A61F 6/225 128/830 |
| 6,887,266 | B2 | 5/2005 | Williams et al. |
| 7,115,691 | B2 | 10/2006 | Alvarado et al. |
| 7,208,550 | B2 | 4/2007 | Mather et al. |
| 7,217,744 | B2 | 5/2007 | Lendlein et al. |
| 7,611,524 | B1 | 11/2009 | Maitland et al. |
| 8,177,738 | B2 * | 5/2012 | Schmieding ........... A61M 1/02 604/187 |
| 8,360,064 | B2 * | 1/2013 | Swann .................. A61B 17/42 128/830 |
| 9,585,784 | B2 * | 3/2017 | Matthiassen ......... A61F 5/4404 |
| 2002/0016613 | A1 | 2/2002 | Kurz et al. |
| 2002/0052613 | A1 | 5/2002 | Ferrera et al. |
| 2002/0161397 | A1 | 10/2002 | Mathews et al. |
| 2002/0173839 | A1 | 11/2002 | Leopold et al. |
| 2002/0183629 | A1 | 12/2002 | Fitz |
| 2003/0014075 | A1 | 1/2003 | Rosenbluth et al. |
| 2003/0066533 | A1 | 4/2003 | Loy |
| 2003/0083735 | A1 | 5/2003 | Denardo et al. |
| 2003/0149470 | A1 | 8/2003 | Alvarado et al. |
| 2003/0153972 | A1 | 8/2003 | Helmus |
| 2003/0199919 | A1 | 10/2003 | Palmer et al. |
| 2004/0030062 | A1 | 2/2004 | Mather et al. |
| 2004/0091543 | A1 | 5/2004 | Bell et al. |
| 2004/0122174 | A1 | 6/2004 | Mather et al. |
| 2004/0193246 | A1 | 9/2004 | Ferrera |
| 2005/0021074 | A1 | 1/2005 | Elliott |
| 2005/0033163 | A1 | 2/2005 | Duchon et al. |
| 2005/0038460 | A1 | 2/2005 | Jayaraman |
| 2005/0171572 | A1 | 8/2005 | Martinez |
| 2005/0212630 | A1 | 9/2005 | Buckley et al. |
| 2005/0234540 | A1 | 10/2005 | Peavey et al. |
| 2006/0116711 | A1 | 1/2006 | Elliott et al. |
| 2006/0025852 | A1 | 2/2006 | Armstrong et al. |
| 2006/0030933 | A1 | 2/2006 | DeLegge et al. |
| 2006/0036045 | A1 | 2/2006 | Wilson et al. |
| 2006/0036280 | A1 * | 2/2006 | French ............ A61B 17/12022 606/200 |
| 2006/0041089 | A1 | 2/2006 | Mather et al. |
| 2006/0079926 | A1 | 4/2006 | Desai et al. |
| 2006/0095134 | A1 | 5/2006 | Trieu et al. |
| 2006/0116713 | A1 | 6/2006 | Sepetka et al. |
| 2006/0129232 | A1 | 6/2006 | Dicarlo et al. |
| 2006/0142789 | A1 * | 6/2006 | Lehman ........... A61B 17/00234 606/153 |
| 2006/0142794 | A1 | 6/2006 | Lendlein et al. |
| 2006/0206140 | A1 | 9/2006 | Shaolian et al. |
| 2006/0213522 | A1 | 9/2006 | Menchaca et al. |
| 2006/0241682 | A1 | 10/2006 | Kurz |
| 2006/0241686 | A1 | 10/2006 | Ferrera et al. |
| 2006/0280768 | A1 | 12/2006 | Hwang et al. |
| 2007/0016233 | A1 | 1/2007 | Ferrera et al. |
| 2007/0083226 | A1 | 4/2007 | Buiser et al. |
| 2007/0104752 | A1 * | 5/2007 | Lee .................. A61B 17/12022 424/422 |
| 2007/0141339 | A1 | 6/2007 | Song et al. |
| 2007/0142893 | A1 | 6/2007 | Buiser et al. |
| 2007/0233037 | A1 | 10/2007 | Gifford, III et al. |
| 2008/0004692 | A1 | 1/2008 | Henson et al. |
| 2008/0082176 | A1 | 4/2008 | Slazas |
| 2008/0097508 | A1 | 4/2008 | Jones et al. |
| 2008/0109057 | A1 * | 5/2008 | Calabria ......... A61B 17/12022 623/1.11 |
| 2008/0114391 | A1 | 5/2008 | Dieck et al. |
| 2008/0147111 | A1 | 6/2008 | Johnson et al. |
| 2008/0183206 | A1 * | 7/2008 | Batiste ...................... A61F 2/01 606/200 |
| 2008/0195139 | A1 | 8/2008 | Donald et al. |
| 2008/0281405 | A1 | 11/2008 | Williams et al. |
| 2008/0312733 | A1 | 12/2008 | Jordan |
| 2009/0054905 | A1 * | 2/2009 | Levy ................ A61B 17/12022 606/108 |
| 2009/0056722 | A1 | 3/2009 | Swann |
| 2009/0099647 | A1 | 4/2009 | Gimsdale et al. |
| 2009/0112251 | A1 | 4/2009 | Qian et al. |
| 2010/0160953 | A1 | 6/2010 | Ngo et al. |
| 2011/0196487 | A1 | 8/2011 | Badawi et al. |
| 2013/0035665 | A1 | 2/2013 | Cully et al. |

FOREIGN PATENT DOCUMENTS

| | | |
|---|---|---|
| JP | 2001520085 A | 10/2001 |
| WO | 1994/06503 A1 | 3/1994 |
| WO | 2000/62711 A1 | 10/2000 |
| WO | 2004/110313 A1 | 12/2004 |
| WO | 2008/051254 A1 | 5/2008 |
| WO | 2010/135352 A1 | 11/2010 |
| WO | 2011/084536 A2 | 7/2011 |

OTHER PUBLICATIONS

Author Unknown, "0.18 and 0.035 Fibered Platinum Coils", Boston Scientific (www.bostonscientific.com), Jan. 2010, pp. 1.
Author Unknown, "Brain Aneurysm Treatment", Boston Scientific (www.bostonscientific.com), Jan. 2010, pp. 2.
Author Unknown, , "Matrix2 Detachable Coils, Occlusion is only the beginning", Boston Scientific (www.bostonscientific.com), Jan. 2010, pp. 1-8.
Author Unknown, "Neurovascular Intervention", Boston Scientific (www.bostonscientific.com), accessed Jan. 2010, pp. 2.
Author Unknown, "Shape Memory Therapeutics Receives Texas Emerging Technology Fund Award", Biomedical Engineering, Texas A&M University, Oct. 21, 2009, pp. 2.

(56) References Cited

OTHER PUBLICATIONS

Author Unknown, "VortX 18 and 35 Vascular Occlusion Coils", Boston Scientific (www.bostonscientific.com), accessed Jan. 2010, pp. 2.
Codman & Shurtleff, Inc., "Trufill DCS Orbit Detachable Coil System", http://www.codman.com/DePuy/products/Products/neurovascular/trufillorbit/index.html, accessed Jan. 2010.
De Nardo, Luigi et al., "Shape memory polymer foams for cerebral aneurysm reparation: Effects of plasma sterilization on physical properties and cytocompatibility", www.sciencedirect.com, ActaBioMaterialia, 2009, pp. 1508-1518.
EV3 Inc., "Embolic Coils", ev3 Inc., http://www.ev3.net/neuro/intl/embolic-coils/nxt-detachable-coils5391.htm, accessed Jan. 2010, pp. 1.
Gall, Ken et al., "Thermomechanics of the Shape Memory effect in polymers for biomedical applications", J. Biomed Mater Res 73A, 2005; 73(3): 339-348, Apr. 1, 2005 (www.interscience.wiley.com) Wiley Int Science.
Hampikian, Janet M. et al., "Mechanical and radiographic properties of a shape memory polymer composite for intracranial aneurysm coils", Materials Science and Engineering C 26, (2006), pp. 1373-1379.
Heaton, Brian C., "A Shape Memory Polymer for Intracranial Aneurysm Coils: An Investigation of Mechanical and Radiographic Properties of a Tantalum-Filled Shape Memory Polymer Composite", Georgia Institute of Technology, Jul. 2004, pp. 1-60.
Maitland, D. J. et al., "Photothermal properties of shape memory polymer micro-actuators for treating stroke", Las. Surg. Med., vol. 30, No. 1, 2002, pp. 1-11.
Maitland, Duncan J. et al., "Design and Realization of Biomedical Devices Based on Shape Memory Polymers", Materials Research Society, Spring 2009.
Maitland, Duncan J. et al., "Prototype laser-activated shape memory polymer foam device for embolic treatment of aneurysms", Journal of Biomedical Optics, May/Jun. 2007, vol. 12(3), pp. 030504-1-3.
Metzger, M. F. et al., "Mechanical properties of mechanical actuator for treating ischemic stroke", Biomed. Microdevices, vol. 4, No. 2, Nov. 2, 2002, pp. 89-96.
Microvention Terumo, "HydroSoft", http://www.microvention.com/Products/Coils/HydrogelProducts/HydroSoft/tabid/70/default.aspx, accessed Jun. 8, 2010, pp. 2.
Microvention Terumo, "MicroPlex Coil System", http://www.microvention.com/Products/Coils/MicroPlexProducts/tabid/63/default.aspx, accessed Jun. 8, 2010, pp. 1.
Microvention Terumo, "The Facts About HydroCoil", http://www.microvention.com/Products/Coils/HydrogelProducts/HydroCoil/tabid/69/Default.aspx, accessed Jun. 8, 2010, pp. 2.
Micrus Endovascular, "Enhanced Embolic Coils for the Treatment of Cerebral Aneurysms", http://www.micrusendovascular.com/products/cerebyte_intl.asp?ln=h, accessed Jan. 2010, pp. 3.
Neurovasx, "ePAX", http://www.neurovasx.com, accessed Jan. 2010, pp. 1.
Small, IV, Ward et al., "Biomedical applications of thermally activated shape memory polymers", J. Mater. Chem., Mar. 2, 2010, 20, pp. 3356-3366.
University of California, Davis , "Development of aneurysm treatment using laser-deployed shape memory polymer foams", http://cbst.ucdavis.edu/research/aneurysm-treatment/development-of-aneurysm-treatment-using-laser-deployed-shape-memory-polymer-foams, May 12, 2010, 3 pages.
Wilson, Thomas S. et al., "Shape Memory Polymer Therapeutic Devices for Stroke", Smart Medical and Biomedical Senso Technology, III, Proc. of SPIE, vol. 6007 (2005), pp. 60070R-1-8.
Yakacki, Christopher J. et al., "Optimizing the thermomechanics of shape-memory polymers for biomedical applications", Material Research Society Symposium Proceedings, vol. 855E, Dec. 1, 2004, pp. 106-111.
Canadian Intellectual Property Office, Office Action dated Apr. 28, 2017 in connection with Canadian Patent Application No. 2,903,834, 3 pages.
European Patent Office, Communication pursuant to Rule 164(2)(b) and Article (94)(3) EPC dated Jul. 7, 2017 in connection with European Patent Application No. 14720353.3, 7 pages.
First Office Action issued for Japanese Patent Application No. 2016-502101, dated Oct. 31, 2017 (12 pages).

* cited by examiner

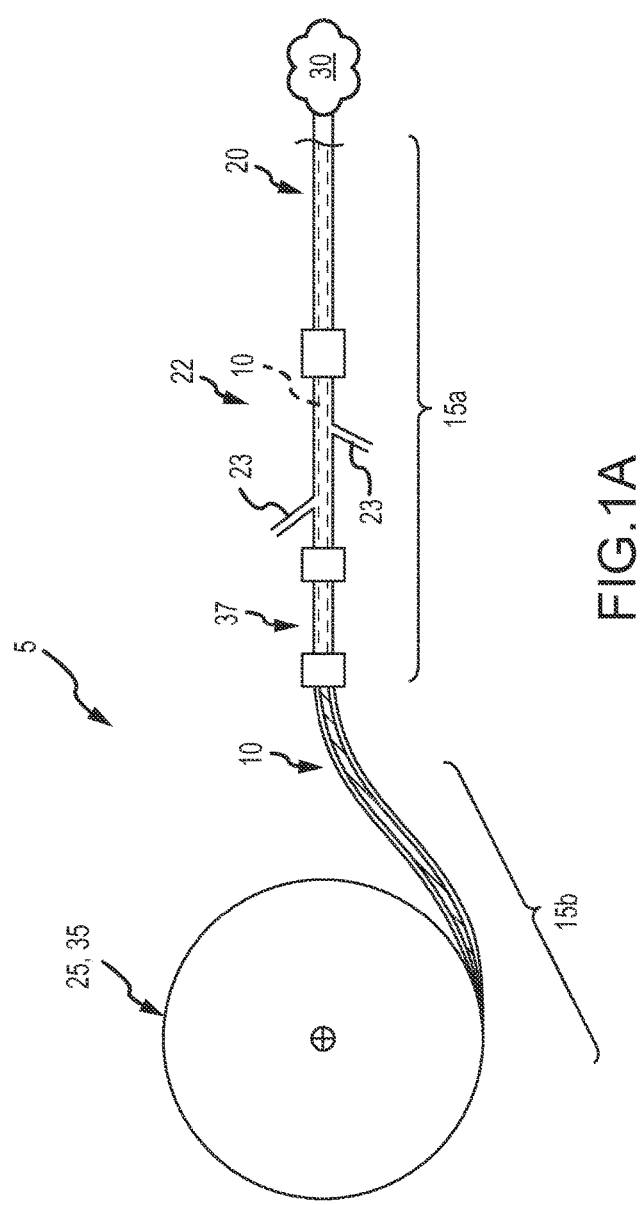

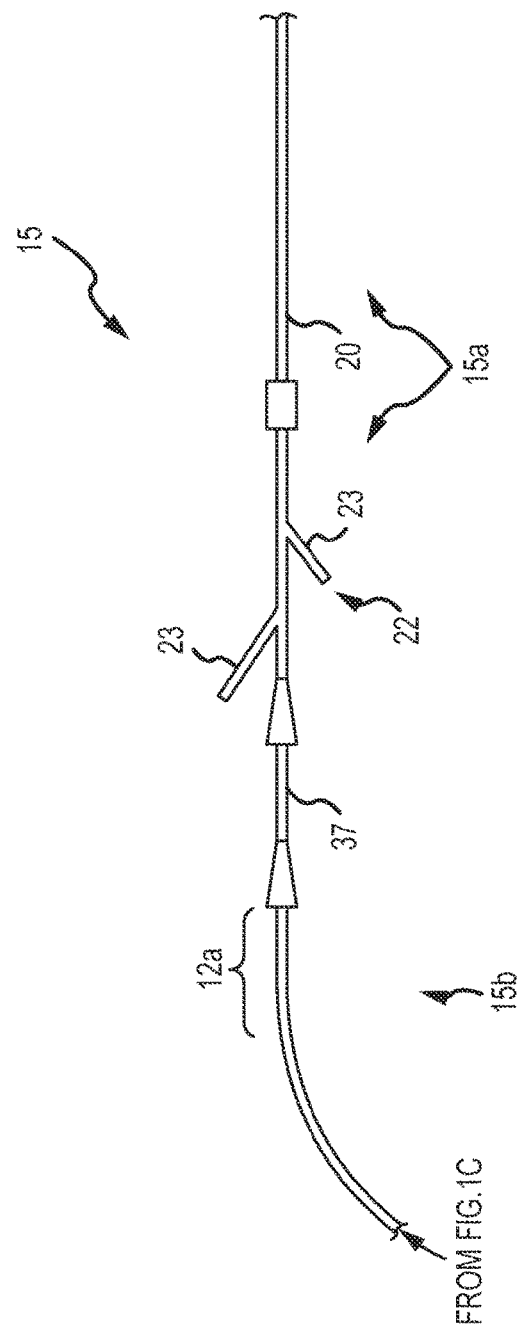

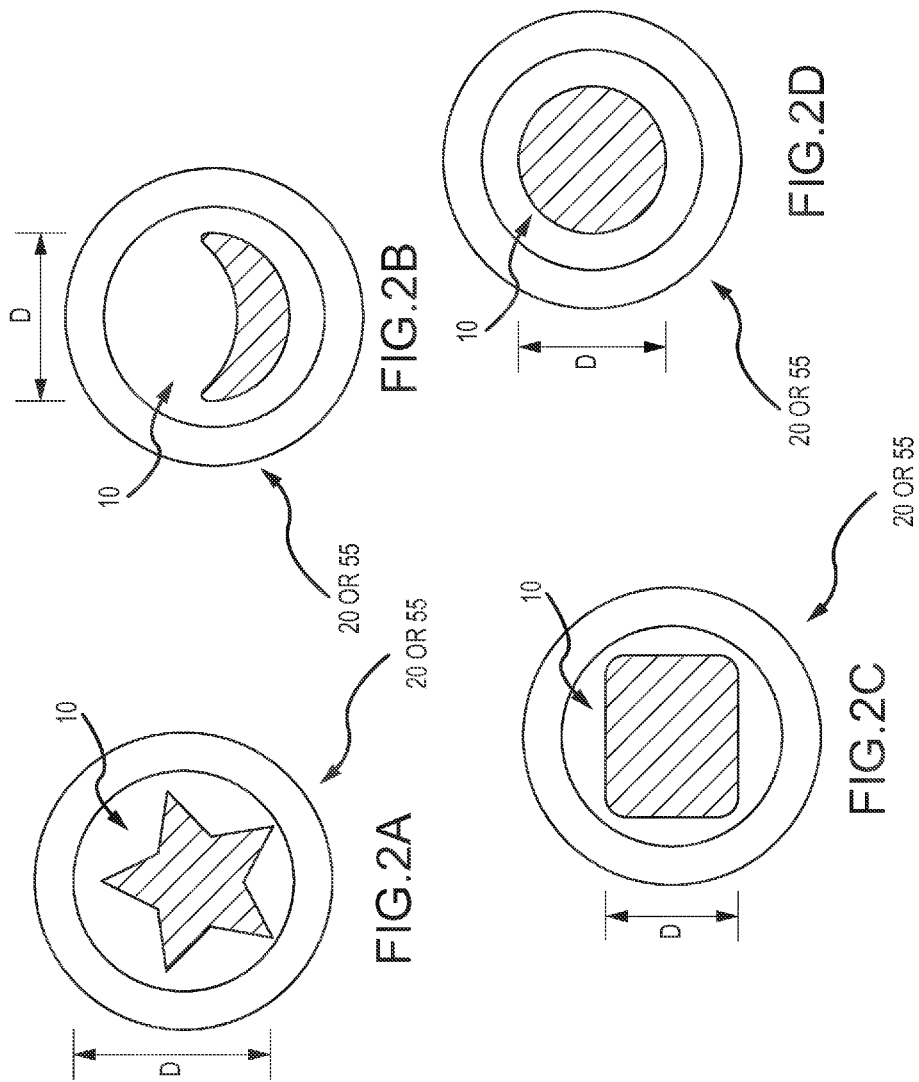

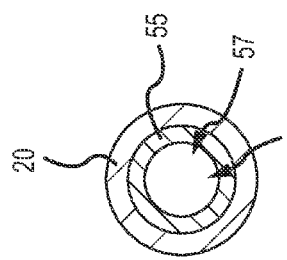
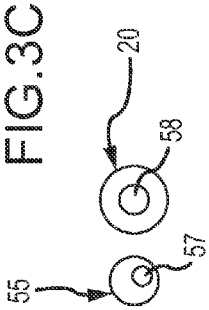
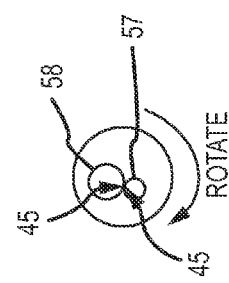
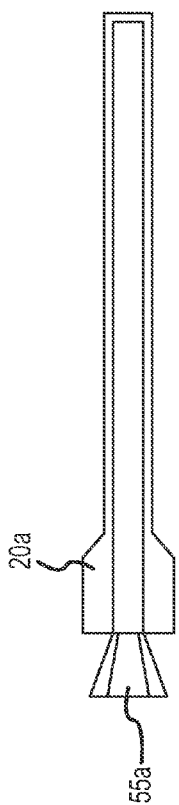

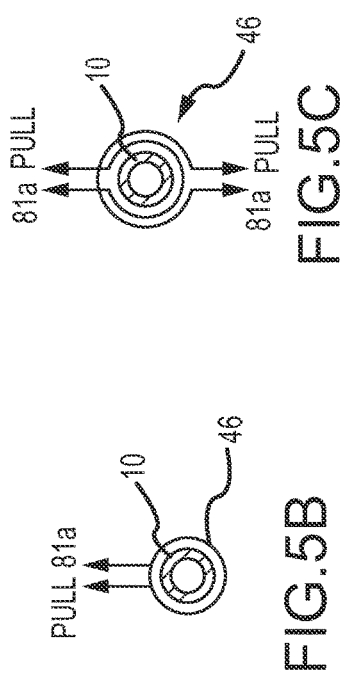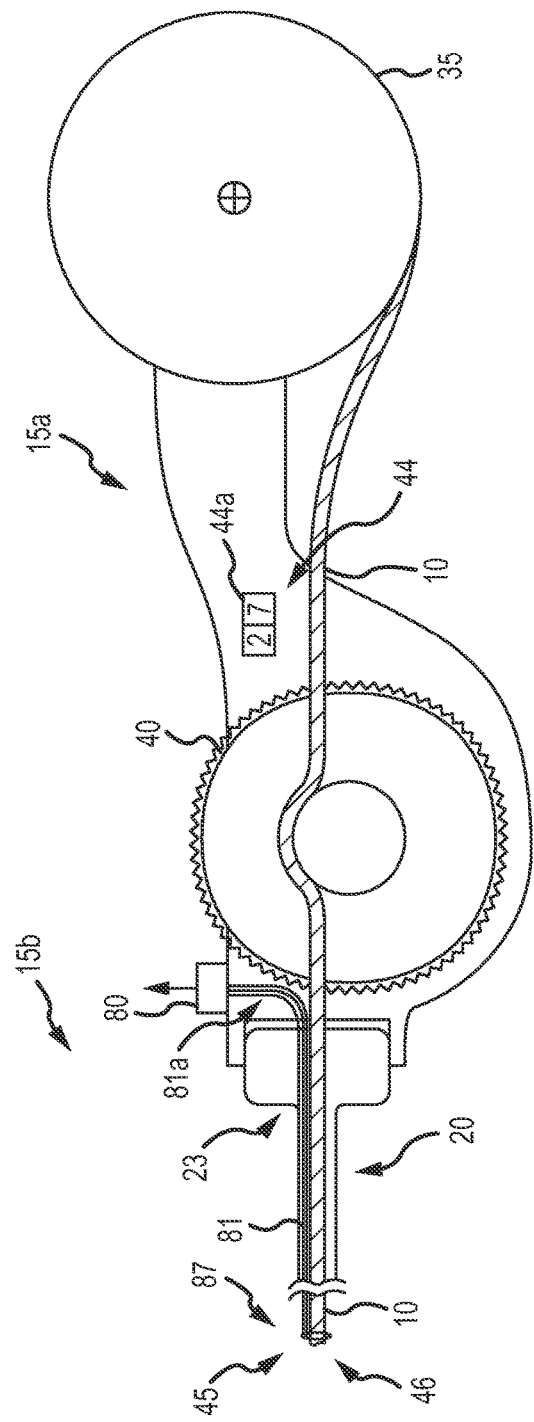

CONTINUOUS EMBOLIC COIL AND METHODS AND DEVICES FOR DELIVERY OF THE SAME

CROSS REFERENCE TO RELATED APPLICATIONS

This application claims the benefit of priority of U.S. Application No. 61/779,360, filed Mar. 13, 2013 and entitled Continuous Embolic Coil and Methods and Devices for Delivery of the Same, which is hereby incorporated by reference as though fully set forth herein.

The following applications are related to the present disclosure: PCT/US11/046829, filed Aug. 8, 2011 and entitled "Radiopaque Shape Memory Polymers for Medical Devices"; and U.S. patent application Ser. No. 13/262,546 filed Sep. 30, 2011 and entitled "Vascular Occlusion Devices", each of which are hereby incorporated by reference as though fully set forth herein.

TECHNICAL FIELD

The disclosure relates generally to implantable devices for therapeutic treatment, and more particularly relates to an endoluminally delivered device for vascular occlusion and methods and devices for delivery of the same.

BACKGROUND

During many clinical procedures, a physician requires the reduction or complete stoppage of blood flow to a target region of the patient's body to achieve therapeutic benefit. A variety of devices are available to provide occlusion of blood vasculature including embolic coils, metal-mesh vascular plugs, beads, particles and glues. Interventional radiologists and vascular surgeons (and similar medical specialists) draw from these therapeutic options based upon the specific need and confidence of a rapid and effective occlusion given the attributes and deficiencies of each of these options. These devices may be used to occlude vasculature in situations requiring treatment, for example, of arteriovenous malformations (AVMs), traumatic hemorrhage, fistulae, some aneurysm repair, uterine fibroid, and tumor embolization. For these clinical treatments, the blood flow through a target section of a blood vessel, aneurysm or defect must be stopped. The device is introduced into the blood vessel through a sterile delivery catheter or sheath using common percutaneous access outside the body. The delivered, artificial device induces an initial reduction of blood flow through a simple mechanical blockage which in turn triggers the body's natural clotting process to form a more complete blockage comprised of the thrombus adhered to the device.

One specific clinical purpose is to fill an aneurysm space, or sack, that resides behind an endograft for repair of Abdominal Aortic Aneurysms. The endograft is intended to isolate a weakened vessel wall in the aorta from blood pressure and thereby reduce the risk of rupture. While the graft may successfully isolate the aortic blood flood, side branches and feeders may connect into the aneurysm sack and continue to present blood pressure on the weakened vessel wall. One attempt for resolution is to access this sack behind the endograft and fill this space with embolic coils. Access may be performed through a catheter, trocar or needle cannula, the latter may be through tissue by puncturing the aneurysmal wall. As this space can be relatively large, independent coils of defined length can only contribute a small percentage of displacement. In order to fill this space, a very large number of metallic coils may be used resulting in a very large metal mass to reduce blood flow and ultimately achieve flow stasis in the sack behind the graft. This is very costly, requires considerable x-ray exposure to both physician and patient, and the resulting metal mass can detrimentally affect post procedure patient imaging with either CT or MR scanning.

Current embolic coils are made from biocompatible materials and provide a biodurable, stable blockage of blood flow. The coils anchor to the vessel wall or aneurysm through radial compliance pressing onto the vessel wall surface. Coils must be suitably anchored to avoid migrating downstream under the forces of the blood flow, which can be significant in larger vasculature. Embolic coils are often shaped for flexibility through a primary coiling and for achieving a "coil pack" within the vessel through a secondary, sometimes complex, three dimensional shape. The coil pack appears as a relatively random crossing and intertwining of the coil within the vessel. After slowing the blood flow, over time, a clot forms around the embolic coil and blood flow through the section is completely blocked.

Typical embolic coils are formed by two major steps: 1) a wire of platinum or other bio-compatible material is wound into a spring, forming what is commonly referred to as a primary coil; and 2) the primary coil is in turn wound around a mandrel having a more complex shape and is subject to high heat to yield a secondary coil. The secondary coil is thus a coiled wire of complex shape or, if helical, a larger curl diameter. Coils can also be provided in multiple secondary shapes including multiple helical curl diameters and in tapered helical shapes with one end employing a large curl diameter and the other end a small curl diameter. These metal coils are straightened, within their elastic bending limit, so as to be advanced into a delivery catheter and pushed down the catheter by a guide wire, pusher, or a detachable pre-attached pusher, until expelled into the vessel. Often, polymeric fibers are applied to the metallic coils in order to increase a thrombus response in addition to providing a scaffolding for thrombus to adhere to and be retained on the coil.

Embolic coils are sized to fit within the inner lumen of a catheter or sheath to be delivered to the target occlusion site individually and sequentially. Typically, a physician will use multiple coils of discrete lengths to occlude a single vessel and, in some cases, especially for larger blood vessels (above 5 mm or so), the physician may use a significant number of coils to achieve cessation of blood flow. To complete an occlusion procedure with embolic coils, the physician must sequentially reload the catheter with several individual coils until he/she has determined the occlusion is sufficient. The physician typically determines whether sufficient coils have been deployed by assessing the level of occlusion of the vessel flow by using contrast media in concert with typical medical imaging techniques. This "place and assess" method can extend the medical procedure time, expose the patient to increased levels of contrast agent, and expose both the patient and the physician to increased radiation through extensive imaging.

Embolic coils are also known for challenges in achieving precise vascular placement. Many of these coils are simply pushed out of the end of a delivery catheter. The final coil pack location is dependent upon whether the coil has been properly sized before deployment and whether the coil was properly anchored into a side vessel/branch as prescribed by several of the coil manufacturers for greater confidence in the final position of the coil packs. Both of these techniques require a high level of physician skill if there is a desire to accurately position both the distal and proximal faces of the coil pack in a vessel using sequential, pushable coils. Some of the coil manufacturers provide a detachable coil—a device that encompasses a coil of discrete length, removably attached to a second delivery system or control wire. At the physician's discretion a placed coil can be released from a delivery control wire. If the coil is not in the proper location it can be retracted and replaced if needed to achieve better position before release. Only the proximal end of the coil is attached to the control wire, resulting in only indirect control of the position of the coil pack's distal face.

Using coils for embolization can present other unique challenges. Voids in the coil pack, developed either during the procedure or post-operatively, can cause channels and resulting blood flow in an unintended area. This condition is typically referred to as recanalization. Depending upon the significance of the condition (e.g., internal hemorrhage), retreatment or surgical intervention may be necessary. The sequential use of independent coils of fixed lengths can be a very time consuming procedure where the intended target is a large vessel. An intraoperative outcome may appear stable and occluded, but greater certainty could be achieved by placing one or more additional coils. However, the challenges of deploying one additional coil to further increase the coil pack density may not be deemed desirable given the coil cost and time involved with placement. The ability to quickly and reliably develop a consistently dense coil pack in a vessel is an important characteristic of a successful vascular occlusion product or aneurysm filling device.

In addition, independent embolic coils can be easily misplaced. Embolic coils may either be injected through a delivery catheter with a syringe filled with saline, pushed by an independent guide wire, or deployed with a detachable pusher that is only connected to the coil via its proximal end. The coil pack shape is dependent upon the successful placement of the initial coil and the ability to engage the subsequent coils in an intermixed and tangled mass of high density. Accordingly, coils can easily be misplaced should the initial coil not land correctly or be slightly undersized to the target vessel and slip beyond the target location. As such, embolic coil packs are known for a high propensity of being elongated in overall size. While these devices have been employed clinically for years and the technique is generally accepted, coils present significant challenges when attempting to embolize in a very precise or limited section of vasculature.

Metal mesh vascular plug devices have also been developed and commercialized to achieve vascular occlusion. These devices achieve occlusion with a single deployment using a metal mesh to provide mechanical flow blockage and, after some time, thrombus forms and a complete occlusion results. When deployed, these devices assume the form of metal mesh balloons or baskets, with one or more lobes contacting the vascular wall, but with defined proximal and distal faces. With occlusion occurring after a single device deployment, these products address many of the deficiencies of embolic coils. However, due to the porosity of the mesh basket and the lack of the polymeric fibers used in coils, the metal mesh plugs have been shown to take longer to achieve occlusion than a properly placed embolic coil pack. Further, the fixed shape of these devices makes them unattractive for use in odd-shaped spaces such as an aneurysm sack that occurs behind an endograft stent.

Further, these metal mesh devices are relatively stiff due to their construction and have limited ability to traverse sharp turns found in catheters that have been placed in a highly tortuous vascular path. The mesh is collapsed into a narrow tube-like shape for introduction and deployment through a delivery catheter or sheath before expanding into the balloon like shape upon deployment. This narrow tube-like shape allows the device to be delivered in the central lumen of small catheters or sheaths similar to coils. However, when the mesh is collapsed, it elongates and becomes a fairly rigid tubular structure. Thus, while being capable of entry into a small delivery catheter, metal mesh devices have limited ability to traverse sharp turns found in catheters that have been placed in a highly tortuous path to reach the target vessel for occlusion. Subsequently, the advantages of a single occlusion device are offset by the slow and incomplete occlusion performance and the limited application to occlusion target sites that are less tortuous to access.

The information included in this Background section of the specification, including any references cited herein and any description or discussion thereof, is included for technical reference purposes only and is not to be regarded subject matter by which the scope of invention is to be bound.

SUMMARY

An occlusion system for occluding a target vessel or filling an aneurysmal space is disclosed herein. The occlusion system may include a continuous embolic coil and may include a delivery device including a first end and a second end. The second end may include a first tubular delivery body including a proximal end, a distal end, and a cutting mechanism positioned in or coupled to the first tubular delivery body. The first tubular delivery body defines a lumen through which the continuous embolic coil is deployed into a target vessel to be occluded or an aneurysmal space to be filled and the cutting mechanism is configured to cut the continuous embolic coil once a desired length of the continuous embolic coil is deployed. In some aspects, the continuous embolic coil is a radiopaque polymer coil. In some aspects, the continuous embolic coil is a shape memory polymer coil. The first tubular delivery body is a catheter or sheath. In some aspects, the first end of the delivery device is coupled to a needle tube/hub introducer configured to receive the continuous embolic coil. In some aspects, the system further includes a coil dispenser coupled to the needle tube/hub introducer and the coil dispenser includes the single continuous embolic coil. The coil dispenser may further include a coil shaped channel around which the continuous embolic coil is wound and held within the coil dispenser until deployment. In some aspects, the system may further include an actuation mechanism to advance and/or retract the continuous embolic coil through the delivery device. The actuation mechanism may be a thumb wheel or a friction wheel. In some aspects, the cutting mechanism is positioned at the proximal end of the first tubular delivery body. In one aspect, the cutting mechanism may be a blade positioned at a hub coupled to the proximal end of the first tubular delivery body and the blade is deployed into the continuous embolic coil to cut the continuous embolic coil by an actuator button. In some aspects, the cutting mechanism is positioned at the distal end of the first tubular delivery body. In some aspects the cutting mechanism is a blade or other device including a sharp edge.

In one aspect, the system further includes a second tubular delivery body. The second tubular delivery body may be a cannula. The second tubular delivery body may be positioned within the first tubular delivery body, each tubular body includes a cutting mechanism, and the bodies are configured to rotate in opposite directions relative to each other in order to cut the continuous embolic coil.

In some aspects, the system further includes a second tubular delivery body having a distal end and a proximal end, a cutting mechanism coupled to or integral with the distal end of the second tubular delivery body, and an actuation wire coupled to the cutting mechanism. The continuous embolic coil defines a void space in the first tubular delivery body and the second tubular delivery body is positioned within the void space defined in the first tubular delivery body above or about the continuous embolic coil.

In one aspect, where the cutting mechanism is positioned at a distal end of the first tubular delivery body, the cutting mechanism is a wire garrote. The wire garrote may include one wire or two wires. The system may also include a wire actuation mechanism, wherein a first free end and a second free end of the wire garrote extend axially along the length of the first tubular delivery body, and at least one free end is coupled to the wire actuation mechanism. The system may also include a guide track positioned within the first tubular delivery body and configured to receive the first free end and the second free end of the wire garrote extending axially along the length of the first tubular delivery body.

In another aspect, the system may include a wire actuation mechanism, a second tubular delivery body, and a ring body coupled to a distal end of the second tubular delivery body. A first free end and a second free end of the wire garrote extend axially along the length of the second tubular delivery body and at least one free end is coupled to the wire actuation mechanism. Further, the wire garrote extends about the ring body in a non-deployed state.

Disclosed herein is a delivery device for a continuous embolic coil for occlusion of a target occlusion site. In some aspects, the delivery device includes a first tubular body including a distal end and a proximal end, an introducer body and hub coupled to the proximal end of the first tubular body, and a cutting mechanism coupled to or positioned in the first tubular body. The first tubular body is configured to receive the continuous embolic coil for deployment at the target occlusion site. The first tubular body is a catheter or a sheath. In some aspects, the delivery device includes an actuation mechanism to advance and/or retract the continuous embolic coil through the delivery device.

In one aspect, the cutting mechanism is positioned at the proximal end of the first tubular body. The device may further include an actuator button. The cutting feature is a blade positioned at the hub coupled to the proximal end of the first tubular body, and the blade is deployed by the actuator button into the continuous embolic coil to cut the continuous embolic coil.

In another aspect, the cutting mechanism is positioned at the distal end of the first tubular body. In some aspects the cutting mechanism is a blade or other device including a sharp edge.

In some aspects, the delivery device further includes a second tubular body positioned within the first tubular body. Each tubular body comprises a cutting feature and the bodies are configured to rotate independently of each other in order to cut the continuous embolic coil.

In another aspect, the delivery device further includes a second tubular body, a cutting mechanism coupled to or integral with the distal end of the second tubular delivery body and an actuation wire coupled to the cutting mechanism. The continuous embolic coil defines a void space in the first tubular body and the second tubular body is positioned within the void space defined in the first tubular body above or about the continuous embolic coil.

In some aspects, the cutting mechanism is positioned at the distal end of the first tubular body and the cutting mechanism is a wire garrote. The wire garrote may include one wire or two wires. In one aspect, the delivery device may include a wire actuation mechanism, wherein a first free end and a second free end of the wire garrote extend axially along the length of the first tubular body and at least one free end is coupled to the wire actuation mechanism. The delivery device may further include a guide track positioned within the first tubular body and it is configured to receive the first free end and the second free end of the wire garrote extending axially along the length of the first tubular body.

In some aspects, the delivery device further includes a wire actuation mechanism, a second tubular body, and a ring body coupled to a distal end of the second tubular body. A first free end and a second free end of the wire garrote extend axially along a length of the second tubular body, at least one free end is coupled to the wire actuation mechanism, and the wire garrote extends about the ring body in a non-deployed state.

Disclosed herein is a method of occluding a target occlusion site with a continuous embolic coil. In one aspect, the method includes loading the continuous embolic coil into a delivery device and the delivery device includes a cutting mechanism and deploying the continuous embolic coil at the target occlusion site for a first time through the delivery device. The method further includes determining whether a coil pack formed by the continuous embolic coil is sufficient and deploying the cutting mechanism via a cutting actuation mechanism. The method further includes engaging the continuous embolic coil with the cutting mechanism to cut the continuous embolic coil and disengaging the cutting mechanism from the continuous embolic coil. In some aspects, the method further includes deploying the continuous embolic coil at the target occlusion site for a second time without reloading the delivery device with a second continuous embolic coil. In some aspects, the method further includes moving the delivery device to a second target occlusion site and deploying the continuous embolic coil at the second target occlusion site without reloading the delivery device with a second continuous embolic coil.

Disclosed herein is an occlusion system for occluding a target occlusion site. In one aspect, the system includes a continuous radiopaque embolic coil configured to be cut to length and a delivery device comprising a first end and a second end, the second end comprising a first tubular delivery body including a proximal end and a distal end. The first tubular delivery body defines a lumen through which the continuous embolic coil is deployed into a target occlusion site. In some aspects, the system may further include a cutting mechanism configured to cut the continuous embolic coil once a desired length of the continuous embolic coil is deployed. The cutting mechanism is coupled to or positioned in the proximal end of the first tubular delivery body. In some aspects, the system may further include a coil dispenser. The continuous embolic coil is maintained in and deployed from the coil dispenser.

Disclosed herein is a system for occluding a target vessel or filling an aneurysmal space. In one aspect, the system includes a continuous radiopaque embolic coil configured to be cut to length. In some aspects, the system further includes a coil dispenser or tubular holding body configured to receive, maintain and deploy the continuous embolic coil.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 1A illustrates one embodiment of an occlusion system including a continuous embolic coil and a delivery device, wherein a first end of the delivery device includes a coil dispenser, according to aspects of the present disclosure.

FIGS. 1C and 1D illustrate aspects of the occlusion system of FIG. 1A including a continuous embolic coil and a delivery device, wherein a first end of the delivery device includes a tube holder configured to receive the continuous embolic coil.

FIGS. 2A-2D illustrate various cross sections of an occlusion device that may be used with the occlusion system of FIG. 1A.

FIGS. 3A-3D illustrate an embodiment of the delivery device of FIG. 1A having a first tubular delivery body, such as a catheter or a sheath, and a second tubular delivery body, such as a cannula, and a cutting mechanism at a distal end of the tubular delivery bodies.

FIGS. 4-8G illustrate various embodiments of the delivery device of FIG. 1A where several embodiments of a cutting mechanism are shown which cut the occlusion device or continuous embolic coil at a distal end of one or more tubular delivery bodies of the delivery device.

DETAILED DESCRIPTION

The target anatomy for vascular occlusion (e.g., internal hemorrhage, tumor isolation, aneurysms, AVMs, etc.) present significant anatomical variability and in many cases, accessing this target anatomy requires a significantly tortuous vascular path in which the delivery catheter or delivery sheath has been placed by a physician, such as an interventional radiologist, before deployment of the occlusion device or continuous embolic coil. The occlusion device or continuous embolic coil enters the tubular delivery body, such as a delivery catheter, outside the patient's body and travels down the delivery body to be deployed (expelled) into the target vessel location or aneurysmal space (i.e. the target occlusion site). At that point, the occlusion device or continuous embolic coil forms an expanding coil pack so as to occlude the vessel or fill the space. Therefore, a clinically acceptable occlusion device or continuous embolic coil is flexible to translate along the delivery body and adaptive to the structure and shape it is filling. Further, an acceptable device will anchor to the vessel wall to resist migration from the influence of the lumen flow, e.g., blood, air, bile, etc.

An exemplary occlusion system comprising a continuous embolic coil that is "cut to length" at the end of its deployment into the target vessel or aneurysmal space is disclosed herein. An exemplary delivery device for the continuous embolic coil that provides such a "cut to length" feature is also disclosed. A continuous embolic coil presents several advantages to the clinician. For example, a typical embolic coil occlusion requires several coils to complete. Before deployment, a clinician must estimate the number and length of coils that will be inserted into the target. The typical discrete length coils may result in the physician misjudging the final coil size such that if a coil that is too short, another discrete coil must be used or, if the final chosen coil is too long, the physician is required to retract the final coil, discard it, and replace it with a shorter coil. Further, the individual coils are deployed one at a time. The clinician is required to sequentially reload the coils until a desired coil pack is achieved.

In contrast, a single, continuous coil as disclosed herein requires only a single loading step and may be "cut to length" by a cutting element associated with the delivery device, as discussed in more detail below. The single continuous coil also limits the need to open additional packages of coils due to underestimating the size of coil needed for the application or due to retraction and discarding of the coils because the chosen coils were too long for the application.

Figures 1, 2, 6A:
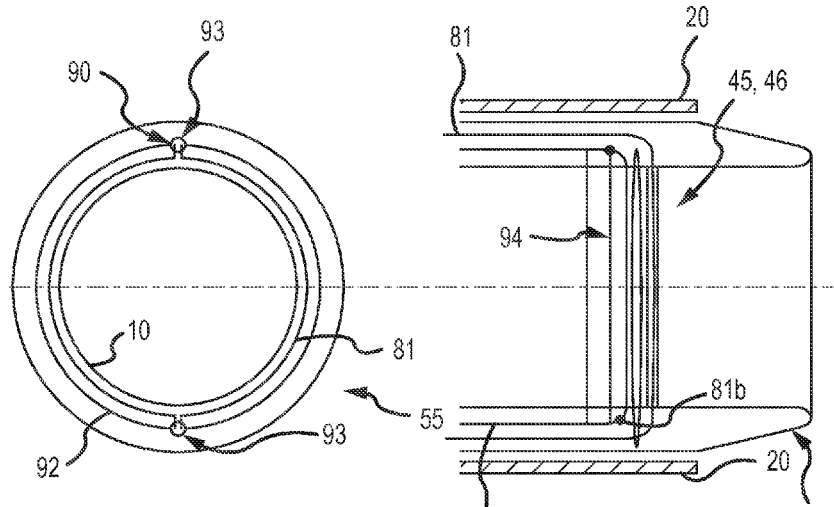

Reference is first made to FIGS. 1A-2D which illustrate some features of the delivery device with a cutting element and some features of the continuous embolic coil. As can be understood from FIGS. 1A-1C, in one embodiment, an occlusion system 5 may include an occlusion device 10, and a delivery device 15. In one embodiment, the occlusion device 10 is a continuous embolic coil 10 of any flexible, biocompatible material. In one embodiment, the continuous embolic coil 10 is a polymer continuous coil. Polymer coils may provide an advantage over other materials in safely cutting their length intraoperatively. In one embodiment, the continuous embolic coil 10 is a shape memory polymer continuous coil. In one embodiment, the continuous embolic coil 10 is a radiopaque polymer coil, such as a coil described in PCT/US11/046829, filed Aug. 8, 2011 and entitled Radiopaque Shape Memory Polymers for Medical Devices. The coil 10 is manufactured in many diameter sizes and shapes to accommodate various target vessels. The polymer coil 10 may be formed with a non-round cross-section which is unique when compared to metal coils that are formed from typical wire-forming processes (e.g., drawn and rolled). Unique cross sections can provide significant advantages to the ability of the polymer coil to fill an aneurysm space or provide stability in position thereby resisting migration due to blood flow, etc. For example, cross sections of the coil 10 may include star-shaped (FIG. 2A), crescent-shaped (FIG. 2B), rounded square (FIG. 2C), or round (FIG. 2D). The exemplary cross-sections of the coil 10 are shown within the delivery device 15. In some embodiments, the effective diameter D of the coil ranges from about 0.007" to about 0.035" in diameter. Such diameters generally correspond to standardized metal coil diameters and common delivery catheter internal diameter sizes.

In one exemplary implementation, the radiopaque polymer coil 10 is manufactured as a unique composite structure, where a second polymer is placed internal to a first polymer forming the bulk of the coil 10 during casting or molding of the polymer coil 10. The second polymer strand may provide several key advantages to the polymer coil 10 including the following: increased stiffness to provide greater radial force at deployment for better anchoring; improved resistance to buckling which assists delivery down a small delivery catheter placed in a tortuous path; and improved strength for retraction back into the delivery catheter if/as needed during deployment in order to modify the placement of the coils, or entirely remove it from the vasculature. Conversely, without the strand, the polymer coil 10 can be very soft and compliant for great compaction and achievement of very high packing factors. Advantageously, fabrication costs of the radiopaque polymer coil 10 are generally low. Either configuration may be trimmed or cut mechanically.

The radiopaque polymer coil 10 may be made with an inherent curl shape to help target how it will deploy and develop a highly dense coil pack in limited anatomical geometry. Coil forms may be fabricated from multiple shapes including, but not limited to, helical, tornado or tapered diameters, three-dimensional framing shapes, two dimensional omega- or D-shapes, or straight (linear shapes). The radiopaque polymer coil 10 may be made from a thermoset, cross-linked polymer that assures that a curled coil shape can be temporarily straightened to place the long coil on a reel or dispensing device (see discussion below) and to transfer the coil 10 through a single delivery catheter lumen, and yet, have high confidence in the coil 10 curling when deployed into the vessel to help form a dense coil pack. Curl diameters can be fabricated across a large spectrum of dimensions including, but not limited to, approximately 2 mm to approximately 25 mm curl diameters.

Returning now to FIGS. 1A-1D, the delivery device 15 of the occlusion system 5 includes at least one tubular delivery body 20, 55, such as a catheter, cannula or delivery sheath 20, 55 and an advance/retract mechanism 25 or other mechanism for pushing the continuous embolic coil 10 out of the tubular delivery body 20, 55 and into the target occlusion site 30. In some embodiments, the delivery device 15 includes an advance/retract mechanism 25 such as a coil-loaded dispenser 35 which may be associated with or include additional features that act or serve as a mechanism to advance the coil 10 into the target occlusion site (such as the coil loaded dispenser 35, see e.g. the reel or bobbin 35 of FIG. 1A, or thumb wheel, see, e.g., the thumb wheel 40 described with respect to FIGS. 5A and 9). In other embodiments, the advance/retract mechanism 25 may be the hand of the surgeon or other practitioner in the surgical suite, such that the coil 10 may be advanced manually (such as by grasping or pushing by hand, see e.g., FIGS. 1C and 1D).

Figure 1B:
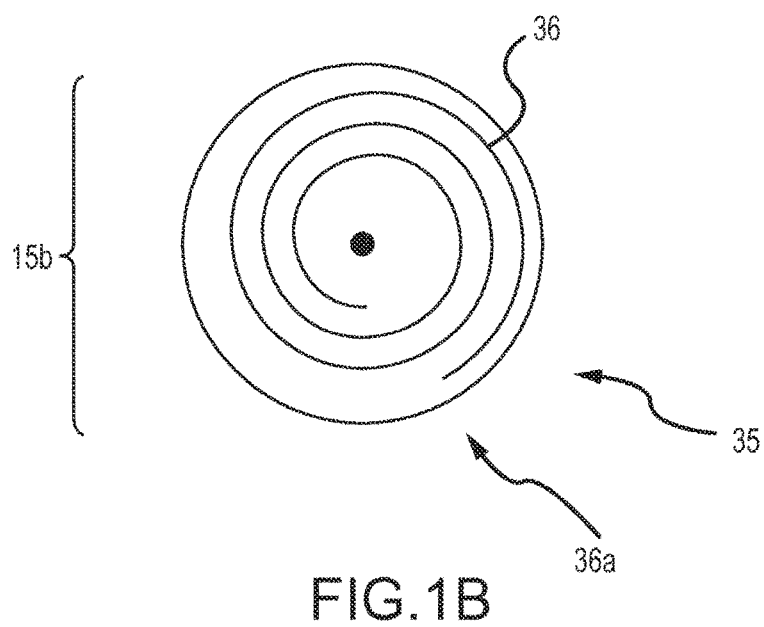
FIG. 1B illustrates an internal view of a second embodiment of a coil dispenser of the delivery device of FIG. 1A, wherein the coil dispenser includes an internal coil channel.

FIG. 1A depicts a first end 15b of the delivery device 15 and includes a coil-loaded dispenser 35. The coil loaded dispenser 35 may be a bobbin or reel upon which the continuous coil 10 is disposed or wound upon. The coil 10 is received on the bobbin or reel and held on the bobbin/reel until deployment. FIG. 1B illustrates a first end 15b of the delivery device 15 and depicts a second embodiment of a coil loaded dispenser 35 wherein a coil shaped channel 36 configured to receive the straightened polymer coil 10 is visible (an outer covering is hidden for clarity). The coil shaped channel 36 is positioned in the coil loaded dispenser 35 and the coil 10 is received in the channel 36 and held within the channel until deployment. The coil loaded dispenser 35 may further include an opening 36a through which the coil 10 may be deployed out of the coil dispenser 35.

Figure 1C:
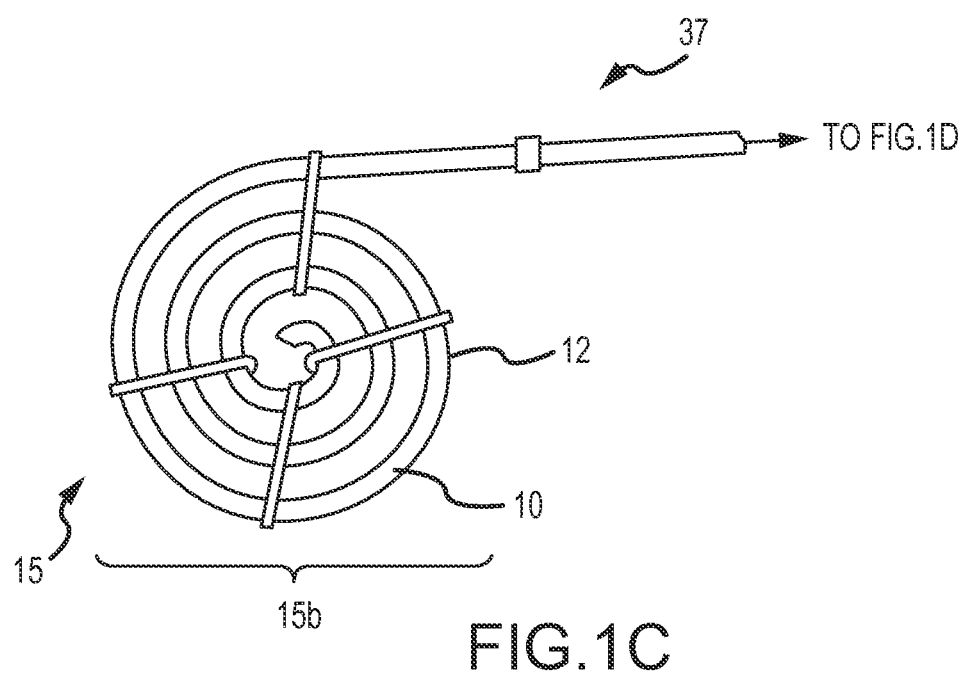

FIG. 1C depicts another embodiment of the first end 15b of the delivery device 15. As can be understood from FIG. 1C, a tubular holding body 12, such as a guidewire or pusher holder tube 12, is maintained in a sterile packaging (not shown) and is configured to hold the straightened coil 10 until deployment. In order to keep the coil 10 in a straighter position in the tube 10, the coil 10 may be manufactured to have less curl shape to it. That is, a coil having shape memory polymer/shape change properties to maintain the straighter (i.e. not curled) shape in the package form may be used in this embodiment. FIG. 1C also depicts the needle tube/hub introducer 37 configured to receive the coil 10 and configured to couple or attach to the catheter 20 to load the coil 10 into the catheter or delivery sheath 20 for delivery to the target occlusion site 30. FIG. 1D illustrates portions of the first end 15b and the second end 15a of the delivery device 15. As can be understood from FIG. 1D, the needle tube/hub introducer 37 is received in the catheter introducer 22, thereby providing a conduit from the tubular holding body 12 to the delivery catheter 20 for the coil 10. The tubular holding body 12 may further include a window 12a or other advancement opening 12a through which a surgeon can access the coil 10 and manually advance the coil 10 from the tubular holding body 12 into the catheter introducer 22. That is, the advance/retract mechanism 25 is the surgeons hand. More specifically, the physician may grasp the continuous coil 10 directly with a gloved hand to either advance or retract the continuous coil 10 and eliminate the need for a separate pusher or wheel for this advancement or retraction function. The catheter introducer 22 may include one or more Y-connectors 23 which serve as tool access points, for example, for injection of a contrast agent to allow the physician to confirm placement and adequacy of the resulting coil pack.

In some embodiments, the polymer coil 10 is manufactured such that a large quantity of the polymer coil 10 is held in a dispenser 35, such as, for example, a bobbin or reel, and the coil is dispensed from the reel in any length. The coil-loaded dispenser 35 eliminates the need for multiple metal occlusion devices because a single polymer occlusion device can be used to service the entire procedure. In addition, one coil-loaded dispenser 35, or reel, may be used to dispense coil lengths for packing at multiple locations in a single patient, provided that the coil is cut between locations, thereby eliminating the need to open separate duplicate packages of coils or coil packages of different lengths during the procedure. For example, this benefit can be specifically realized when coiling gonadal veins to treat varicoceles or for treating chronic pelvic congestion. Both of these procedures require coils to be placed at multiple locations along a single vessel or vessel trunk which may be easily accomplished by using the continuous occlusion system (or aspects of the occlusion system) disclosed herein.

In some embodiments, the coil-loaded dispenser or reel 35 is the mechanism by which the coil is advanced or retracted as deemed appropriate by the physician. In some embodiments, the coil may be provided in various lengths e.g., 20 cm, 50 cm, 100 cm, 150 cm or more. The coil 10 may have variable stiffness along its length and may have a diameter of from approximately 0.010" to approximately 0.035/0.038". The coil 10 may be manufactured to have any appropriate cross-section (see e.g., FIGS. 2A-2D) and may include nylon fibers on a portion of or along the entire length of the coil 10 in order to aid in thrombus formation where advantageous and appropriate. In some embodiments, the coil-loaded dispenser 35 may also include an integrated or separate mechanism or feature for controlling or actuating the coil under slippery or wet conditions commonly found within the sterile field of catheterization procedures. In one exemplary embodiment, the actuation feature 40 may be a simple friction wheel or other mechanical dispenser that moves the coil into the delivery catheter or withdraws the coil from the delivery catheter without the direct physician/ glove contact on the coil. (See, e.g., FIGS. 5A and 9) For certain procedures, such as hemorrhage from trauma and filling of aneurysms, there are medical advantages to allowing for a larger volume of coil to be moved quickly in or out of the delivery catheter. Conversely, for other procedures, such as neurovascular aneurysm repair, there are medical advantages to allowing for very slow, precise movement of the coil into or out of the catheter. The slow or fast deployment of the coils could affect how and what type of coil pack is achieved in the target occlusion site.

Figure 9:
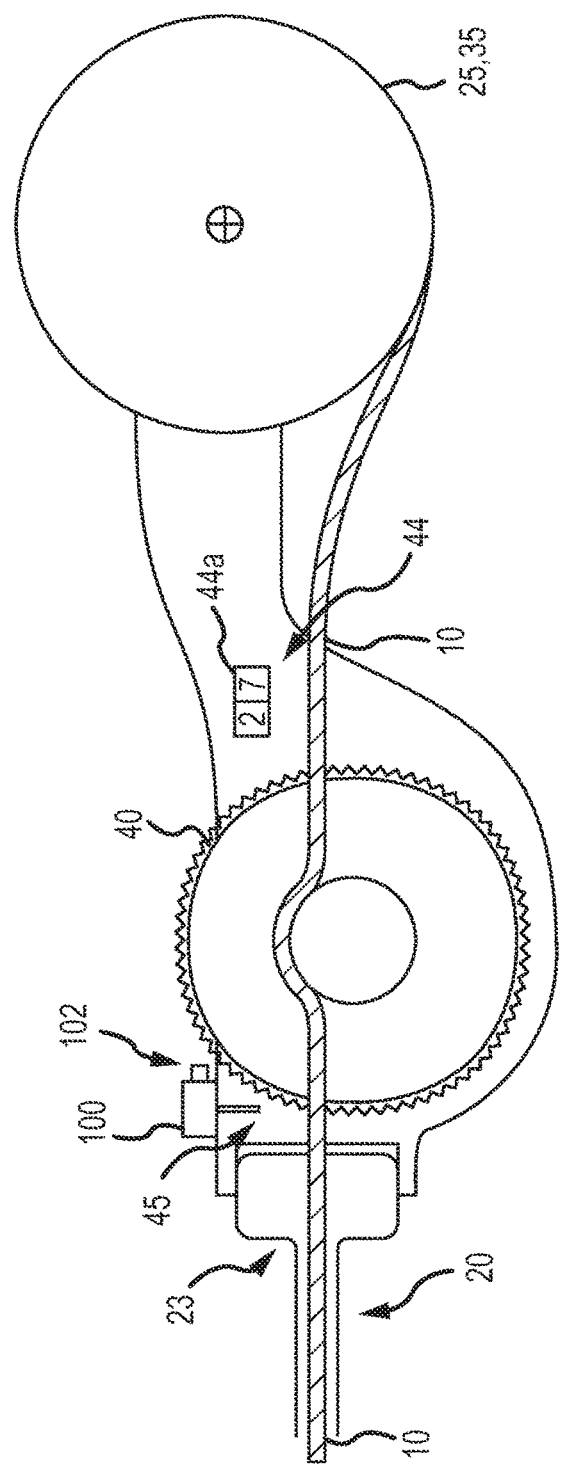
FIG. 9 illustrates an embodiment of the delivery device of FIG. 1A where a cutting mechanism is shown which cuts the occlusion device or continuous embolic coil at a proximal end of a tubular delivery body of the delivery device.

In some embodiments, the coil dispenser 35 may also include or be coupled to a device 44 that provides a display 44a that indicates the amount of coil 10 that has been dispensed from the reel (See, e.g., FIGS. 5A and 9).

Reference is now made to FIGS. 3A-9 for a discussion of a "cut to length" feature or cutting mechanism 45 which may be associated with the second end 15a of the delivery device 15 which includes the tubular delivery body 20, 55, such as a delivery catheter or sheath 20 or cannula 55, of the occlusion system 5. In some embodiments, the cut to length feature or cutting mechanism 45 is located at the distal end of the tubular delivery body 20, 55. In some embodiments, the cut to length feature or cutting mechanism 45 is located at the proximal end of the tubular delivery body 20, 55.

In some embodiments, the system 5 includes a device or feature 45 that provides the ability to intraoperatively trim or cut the polymer coil 10, such as a radiopaque polymer coil 10 to a desired length. Current coils are fabricated in short, independent, discrete lengths that require the physician to estimate the length and quantity of coils that will be needed to occlude the target vessel. Advantageously, the polymer coil or occlusion device 10 described herein requires no such estimation. The currently available short, discrete-length coils often results in the physician misjudging the final coil size—either too short, which requires yet another discrete coil, or too long, which requires that the final coil to be retracted, discarded, and replaced with a shorter coil.

The polymer coil described herein results in a discretionary length of coil having any dimension less than or up to the total length of the material applied to the bobbin/reel. As coil deployment nears its endpoint during the procedure, the physician can carefully deploy "just the right amount" before determining the point at which to cut the coil and end the deployment. Accordingly, the need for opening additional packages due to undersizing coils or retracting and discarding coils that were found to be too long to fit is reduced or eliminated. This flexibility provides for a more predictable and repeatable application of embolic coils for occlusion of a target vessel.

As illustrated in FIGS. 3A-8, in some embodiments, the cut to length feature or cutting mechanism 45 is located at the distal end of the first tubular delivery body 20, such as an outer catheter or sheath 20 and/or at the distal end of the second tubular delivery body 55, such as an inner cannula 55. As shown, the second end 15a of the delivery device 15 comprises a first tubular delivery body 20 (such as an outer catheter sheath 20 and/or a second tubular delivery body 55, such as an inner cannula 55, that incorporates a mechanical cutting mechanism for trimming the polymer coil 10, such as a radiopaque polymer coil (with or without an internal strand) at that end of the tubular delivery body 20, 55. In some embodiments, the cutting mechanism 45 can be used repeatedly without removing and manually reloading the tubular delivery body between uses.

As shown in FIGS. 3A-1 to 3A-2, in one embodiment, the second end 15a of the delivery device 15 comprises an inner cannula 55 or second tubular delivery body 55 coupled to an inner hub 55a and an outer catheter or sheath 20 or first tubular delivery body 20 coupled to an outer hub 20a. In some embodiments, the inner tubular delivery body 55 may be a cannula 55 and the outer tubular delivery body 20 may be a delivery sheath 20. Each of the distal end 51 of the outer sheath or catheter 20 and the distal end 56 of the inner cannula 55 includes a cutting feature 45, such as a mechanical blade or a sharp, defined edge. The hubs 20a, 55a extend outside of the patient where a surgeon may grasp them and rotate them to cut the coil 10. As shown in FIG. 3A-2, the inner tubular body 55 is coaxial with the outer tubular body 20 and the bodies 20, 55 are configured to rotate in opposite directions relative to each other in order to cut the continuous coil 10. That is, the physician rotates the outer tubular body 20 via the outer hub 20a independently of the rotation of the inner tubular body 55 via the inner hub 55a. The distal end 56 of the inner tubular body 55 defines an aperture 57, which may be off-set from the center of the inner or second tubular delivery body 55. The distal end 51 of the outer tubular body 20 defines an aperture 58, which may be off-set from the center of the outer or first tubular delivery body 20.

In use, the continuous embolic coil 10 is loaded into the first tubular delivery body 20 and the second tubular delivery body 55 at the second end 15a of the delivery device 15 in a non-expanded (or pre-deployed or storage) state, e.g., via the needle tube/hub introducer 37 coupled thereto that is configured to receive the coil 10 from, for example, the coil dispenser 35. Once the surgeon has placed the tubular delivery bodies 20, 55 into the proper location, the continuous embolic coil 10 may be delivered by an advance/retract mechanism 25 out of the tubular delivery bodies 20, 55. The straightened continuous coil 10 (in a non-expanded state) is deployed by advancing it down the tubular delivery body 20, 55, using an advance/retract mechanism 25 to deliver it out of the distal ends of the of the tubular delivery bodies 20, 55 at the target occlusion site 30. Once the surgeon determines that a desired amount of coil 10 has been delivered to the target site 30, the surgeon can engage the cutting features 45. As the coil 10 emanates from the inner tubular body 55 that is coaxial with the outer tubular body 20 through the holes or apertures 58, 57 at the respective distal ends 56, 51 that are offset from the center of both the inner and outer tubular bodies 20, 55 (see FIGS. 3B and 3C), the outer tubular body 20 is rotated with respect to the inner tubular body 55, thereby causing the two openings 58, 57 to cross (see FIG. 3D). The sharp, defined edge 45 on each opening 58, 57, act like scissor blades and cut the polymer coil 10. The outer tubular body 20 is rotated back into its original position (see FIG. 3C), thereby aligning the openings 57, 58 to allow for the unobstructed, continued delivery of the coil 10 between cuts. The coil 10 may continue to be delivered to the target site or to a second target site, as desired.

Figure 4:
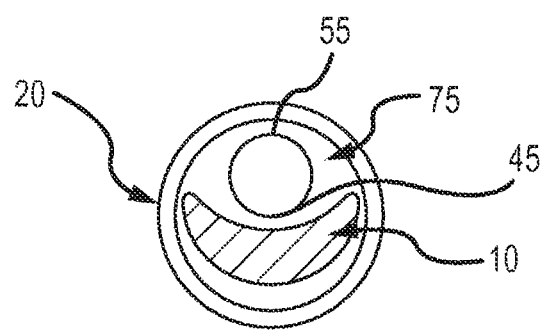

As shown in the distal end cross-section in FIG. 4, in another exemplary embodiment, the delivery device 15 includes a first tubular delivery body 20, such as a catheter 20, and a second tubular delivery body 55, such as a cannula 55. The second tubular delivery body 55 may fit within the first tubular delivery body 20 and may be positioned in a void or hollow space 75 defined in the first tubular delivery body 20 by the continuous coil 10. As shown in FIG. 4, due to the cross-section of the continuous coil 10 (see, e.g., FIGS. 2A-2D), a void or hollow space 75 may be defined between the coil 10 and the first tubular delivery body or catheter 20. The second tubular delivery body or cannula 55 may be positioned within the void 75 such that the cutting mechanism 45 is positioned over or about the coil 10. The second tubular delivery body or cannula 55 includes a cutting mechanism 45, such as a blade or sharp edge disposed at a distal end thereof and an actuator extending within the second tubular delivery body 55 from the proximal end to the distal end, such as an actuation wire 81 (not shown), that is coupled to the cutting mechanism 45 to actuate the cutting mechanism 45 to cut the coil 10.

In use, the second tubular body or cannula 55 with a cutting feature 45 is co-loaded with the occlusion device or continuous embolic coil 10 into the first tubular delivery body 20 at the second end 15a of the delivery device 15 in a non-expanded (or pre-deployed or storage) state, e.g., via the needle tube/hub introducer 37 coupled thereto that is configured to receive the coil 10 from, for example, the coil dispenser 35. Once the surgeon has placed the first tubular delivery body 20 into the proper location, the occlusion device or continuous embolic coil 10 may be delivered by an advance/retract mechanism 25 out of the first tubular delivery body 20. The straightened continuous coil 10 (in a non-expanded state) is deployed by advancing it down the tubular delivery body 20, using an advance/retract mechanism 25, to deliver it out the distal end of the first tubular delivery body 20 at the target occlusion site 30. Once the surgeon determines that a desired amount of coil 10 has been delivered to the target site 30, the surgeon can actuate the second tubular delivery body 55. The surgeon pulls the actuation wire 81 to engage the cutting feature 45, thereby cutting the coil 10. After the coil 10 is cut, the cutting feature 45 is disengaged from the coil 10 by releasing the actuation wire 81. The second tubular delivery body 55 can be withdrawn from the first tubular delivery body 20 or remain in place and the coil 10 can continue to be delivered, unobstructed, to the target site or to a second target site, as desired.

As can be understood from FIGS. 5A-7, in some embodiments, the cutting mechanism 45 may be a wire garrote 46. As shown in FIG. 5A, the first end 15b of the delivery device 15 includes a coil dispenser 35 coupled to a second end 15a of the delivery device that includes a first tubular delivery body 20, such as a delivery catheter or sheath 20, via a catheter/sheath hub 23. The delivery device 15 may include a mechanical advance/retract mechanism 25, such as an actuation mechanism 40, such as a thumb wheel, to advance and retract the coil 10. In other embodiments, and with reference to FIGS. 1C and 1D, the first end 15b of the delivery device 15 may include a manual advance/retract mechanism 25. The delivery device 15 may also include a wire actuation mechanism 80 coupled to one or more wires 81 that are associated with each other to make a cutting mechanism 45, such as a wire garrote 46. In some embodiments, the wires 81 are made of nitinol, stainless steel or other appropriate thin wire. The wire or wires 81 are disposed axially along the length of the first tubular delivery body 20 from the distal end 87 back to the proximal hub 23. At the proximal hub 23, there is a wire actuation mechanism 80 that permits the physician to pull the wire 81 thereby causing the distal end of the garrote 46 to tighten around the polymer coil 10 and subsequently cut through it.

In one embodiment, and as can be understood from FIG. 5B, the wire garrote 46 is comprised of a single wire 81. The single wire 81 extends from the distal end of the first tubular delivery body 20 and encircles the coil 10. The free ends 81a of the wire 81 are coupled to the wire actuation mechanism 80. When the wire actuation mechanism 80 is actuated (e.g., pulled), the free ends 81a transition from a relaxed stated (e.g., they are pulled taut) and the portion of the wire 81 encircling the coil 10 tightens or closes around the coil 10, thereby cutting the coil 10. Once cut, the wire actuation mechanism 80 is released, the free ends 81a transition back to a relaxed state and the portion of the wire 81 encircling the coil 10 loosens or relaxes around the coil 10 such that coil delivery can continue unobstructed by the wire garrote 46.

In another exemplary embodiment, and as can be understood from FIG. 5C, the wire garrote 46 is comprised of at least two wires 81. The wires 81 extend from the distal end of the first tubular delivery body 20 and encircle the coil 10. The free ends 81a of the wires 81 are coupled to the wire actuation mechanism 80. When the wire actuation mechanism 80 is actuated (e.g., pulled), the free ends 81a transition from a relaxed state into a non-relaxed state (e.g., they are pulled taut) and the portion of the wires 81 encircling the coil 10 tighten or close around the coil 10, thereby cutting the coil 10. Once cut, the wire actuation mechanism 80 is released, the free ends 81a transition back to a relaxed state and the portion of the wires 81 encircling the coil 10 loosen or relax around the coil 10 such that coil delivery can continue unobstructed by the wire garrote 46.

In another embodiment, and as can be understood from FIGS. 6A-1 through 6C-2, instead of being positioned in the first tubular delivery body or catheter 20, the wire garrote 46 is positioned in a second tubular delivery body 55, such as a cannula 55, that passes through the first tubular delivery body 20 of the delivery device 15 as described above with respect to FIG. 5A. The second tubular delivery body 55 includes one or more smaller tubular bodies or conduits 90 disposed axially along the length of the second tubular body 55. The conduit(s) 90 define a lumen configured to receive the wire 81. In one embodiment, as shown in FIG. 6A-1, the distal end 92 of the conduit 90 may include a hypotube tip 93 and may optionally include and be coupled to a ring body 94 (see FIG. 6A-2) by any appropriate means, such as welding or an adhesive. In other embodiments, the cannula 55 does not include a ring body 94. The hypotube tip 93 provides structural support to the tip of the tubular body 55 and if included, together with the ring body 94, provides a structure to hold the wire 81 in position and when actuated, prevents the wire 81 from shredding the first tubular delivery body 20 because the wire 81 only engages with the coil 10 and does not engage with the first tubular delivery body 20. In some embodiments, and as indicated in FIG. 6A-2, the distal end 92 of the conduit 90 does not include a hypotube tip 93. A ring body 94 is positioned at a distal end of the cannula 55, and a distal end 81b of the wire 81 is coupled to the ring body 94 by any appropriate means, such as welding or an adhesive. As such, only a single wire 81 comes back to the proximal end of the first end 15b of the delivery device 15. The wire 81 maintains its shape around the ring body 93 based on the shape memory characteristics of the wire 81. The ring body 94 provides structural support to the tip of the tubular body 55 and provides a structure to hold the wire 81 in position and when actuated, prevents the wire 81 from shredding the first tubular delivery body 20 because the conduits 90 do not collapse and the wire 81 only engages with the coil 10 and does not engage with the first tubular delivery body 20.

In one embodiment, the inner diameter of the first tubular delivery body 20 is 0.055", the outer diameter of the second tubular delivery body 55 is 0.053" and the inner diameter of the second tubular delivery body 55 is 0.036". In some embodiments, the second tubular body 55 or cannula 55 may be a double wall cannula having a diameter of 0.017" or a single wall cannula having a diameter of 0.0085". The wire 81 may be 0.001" stainless steel or nitinol wire having an outer diameter of 0.035". The smaller tubular bodies or conduits 90 may be PEEK tubes or PEEK tubes with hypotube tips and, in some embodiments, have a diameter of less than 0.0085".

Figures 1, 6B:
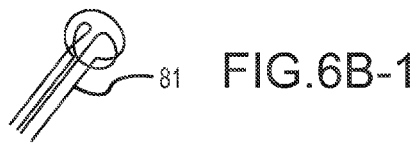

In use, the occlusion device or continuous embolic coil 10 is loaded into the first tubular delivery body 20 and the second tubular delivery body 55 in a non-expanded (or pre-deployed or storage) state, e.g., via the needle tube/hub introducer 37 coupled thereto that is configured to receive the coil 10 from, for example, the coil dispenser 35. The wire(s) 81 are threaded through the conduits 90 before placement of the second tubular delivery body 55 into the first tubular delivery body 20. While the loop of wire 81 that defines the garrote 46 is formed around the ring body 94 (when it is included) prior to insertion, the coil 10 may proceed through the delivery bodies 20, 55 unobstructed until the wire actuation mechanism 80 is engaged. Where a ring body 94 is not present, enough wire 81 is extended from the conduits 90 with hypotube tips 93 such that a single loop (from a single wire 81) or a double loop (from a double wire 81) (i.e. the garrote 46) is formed through which the coil 10 can pass without obstructing delivery of the coil 10. Once the surgeon has placed the tubular delivery bodies 20, 55 into the proper location, the coil 10 may be advanced by an advance/retract mechanism 25, such as an actuation feature 40, out of the delivery bodies 20, 55. Once the surgeon determines that a desired amount of coil has been delivered to the target site, the surgeon engages the wire actuation mechanism 80 to engage the garrote 46, which tightens around the polymer coil, thereby cutting the coil 10 (see FIGS. 6B-1, 6B-2, 6C-1 and 6C-2). FIGS. 6B-1 and 6B-2 depict a garrote 46 having two wires 81 and FIGS. 6C-1 and 6C-2 depict a garrote 46 having a single wire 81.

In one exemplary embodiment, and as can be understood from FIGS. 6B-1 and 6B-2, the wire garrote 46 is comprised of at least two wires 81. The wires 81 extend from the distal end of the second tubular delivery body 55 or cannula 55 and encircle the coil 10. The free ends 81a of the wires 81 are coupled to the wire actuation mechanism 80. When the wire actuation mechanism 80 is actuated (e.g., pulled in the direction indicated by the arrows), the free ends 81a transition from a relaxed state into a non-relaxed stated (e.g., they are pulled taut) and the portion of the wires 81 encircling the coil 10 tighten or close around the coil 10, thereby cutting the coil 10. Once cut, the wire actuation mechanism 80 is released, the free ends 81a transition back to a relaxed state and the portion of the wires 81 encircling the coil 10 loosen or relax around the coil 10 such that coil delivery can continue unobstructed by the wire garrote 46 and the cutting wire 81 is positioned as it was before it was used to cut the coil 10. In another embodiment, the cutting wire 81 is not repositioned back to its relaxed state. Instead, the second delivery body 55 or cannula 55 with wire(s) 81 is replaced after every cut. That is, coil 10 and the used cannula 55 are withdrawn from the first tubular delivery body 20 or catheter 20 and a new cannula 55 is loaded into the catheter 20 and the continuous coil 10 is reloaded into the first and second delivery bodies 20, 55. In another embodiment, the wire(s) 81 and garrote 46 reset after cutting the coil 10 without any physical intervention based on the shape memory properties of nitinol. That is, because the wire(s) 81 are made of nitinol, the wire(s) 81 transition back to a relaxed state following the cut without physical intervention. In another embodiment, the cutting wire 81 is reset or repositioned with a mini-cannula (e.g. a smaller version of the cannula 55). In such an embodiment, the coil 10, after being cut, is retracted from the tubular delivery body(ies) 20, 55. A stiffer cannula having approximately the same diameter as the coil 10 and having a tapered distal end is advanced down the catheter 20 to contact the garrote 46 such that the garrote returns to its original (pre-cutting) position. The stiffer cannula with a tapered end is withdrawn from the catheter 20 and the coil 10 is advanced back down the catheter 20 to continue the coil delivery process.

Figures 1, 2, 6B, 6C:
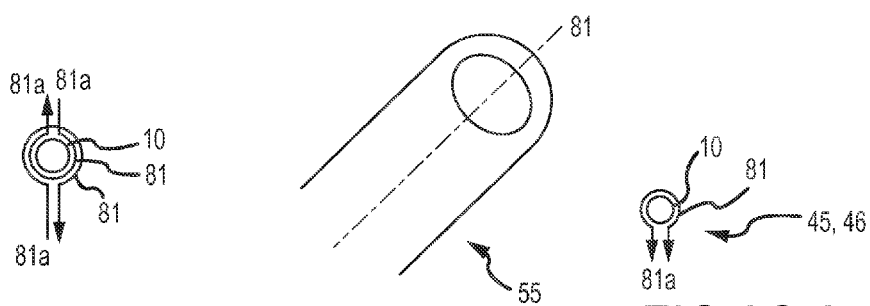

In another exemplary embodiment, and as can be understood from FIGS. 6C-1 and 6C-2, the wire garrote 46 is comprised of a single wire 81. The single wire 81 extends from the distal end of the second tubular delivery body 55 or cannula 55 and encircles the coil 10. The free ends 81a of the wire 81 are coupled to the wire actuation mechanism 80. When the wire actuation mechanism 80 is actuated (e.g., pulled in the direction indicated by the arrows), the free ends 81a transition from a relaxed state into a non-relaxed stated (e.g., they are pulled taut) and the portion of the wire 81 encircling the coil 10 tightens or closes around the coil 10, thereby cutting the coil 10. Once cut, the wire actuation mechanism 80 is released, the free ends 81a transition back to a relaxed state and the portion of the wire 81 encircling the coil 10 loosens or relaxes around the coil 10 such that coil delivery can continue unobstructed by the wire garrote 46.

While FIGS. 6A-1 through 6C-2 describe embodiments related to a second tubular delivery body 55 or cannula 55, it can be appreciated that the first tubular delivery body 20 or catheter 20 may also have smaller tubular bodies or conduits 90 disposed axially along the length of the delivery body 20 and configured to receive the wire(s) 81.

Figure 7:
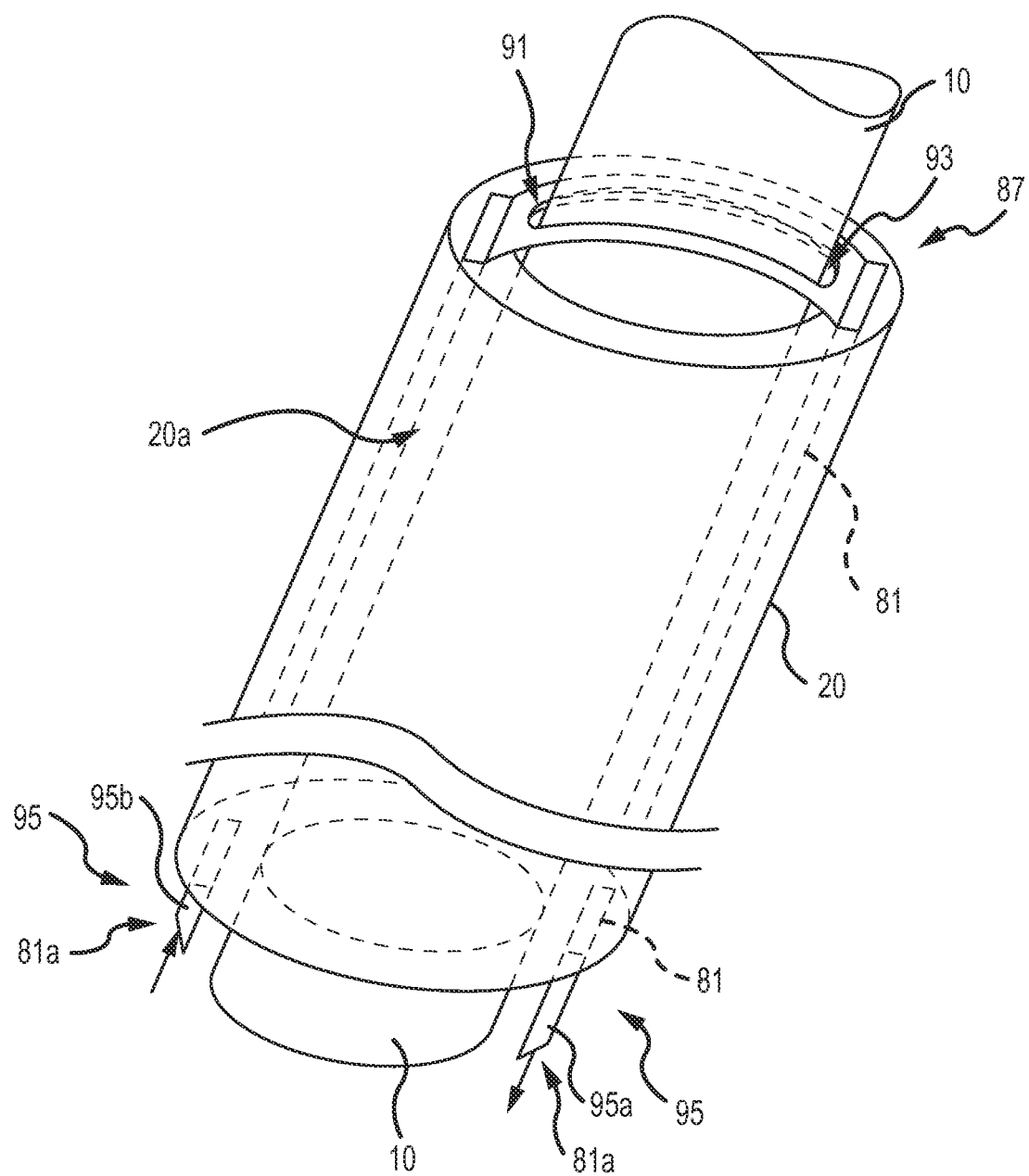

As can be understood from FIG. 7, the first end 15b of the delivery device 15 may be as described above with respect to FIG. 5A. The wire or wires 81 are ribbon-like and are disposed axially along the length of the first tubular delivery body 20 in the wall 20a of the first tubular delivery body 20 or catheter 20 and back to the proximal hub/end 23 of the second end 15a of the device 15. At the proximal/hub end 23, the proximal ends 81a of the ribbon-like wire 81 may act as a wire actuation mechanism 95 in which the ends 81a are pull tabs 95a. The distal end 90 of the ribbon like wire 81 defines an aperture 93 through which the coil 10 can pass unobstructed when the aperture 93 is in an open configuration. The aperture 93 includes a cutting mechanism 45, such as a sharp edge 91 to engage or enclose and tighten (e.g., like a guillotine) around the polymer coil 10 and subsequently cut through it. More specifically, once the surgeon determines that a desired amount of coil has been delivered to the target site, the surgeon engages the pull tab 95a causing the aperture 93 of the ribbon-like wire 81 to close around the coil 10, and specifically a sharp edge 91 of the aperture 93, to engage or enclose and tighten around the polymer coil 10, similar to how the wire garrote 46 described previously or a guillotine will close around a coil, and subsequently cut through it. After the coil is cut, the cutting mechanism 45 is disengaged from the coil 10 by releasing the pull tabs 95a of the wire actuation mechanism 95. Push tab 95b may be used to further release the wire 81 from about the coil 10 by pushing the tab 95b to allow the aperture 93 to further release the coil 10. The surgeon can continue to deploy the coil 10 into the target occlusion site 30 unobstructed by the cutting mechanism 45 as desired. In some embodiments, a ring body 94 as described above with respect to FIG. 6A-2, and others, may be used to provide structure and support to the distal end of the catheter 20. In some embodiments, rather than being disposed in a wall 20a of the catheter 20, conduits 90 as described above but with a cross-section that would complement the ribbon-like wire, may be used to provide a conduit for the axial disposition of the ribbon-like wire.

Figure 8A:
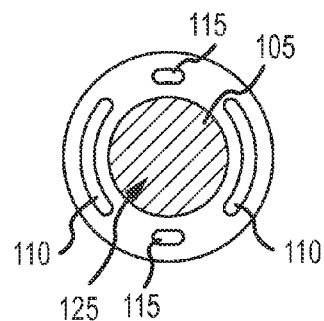
Figure 8B:
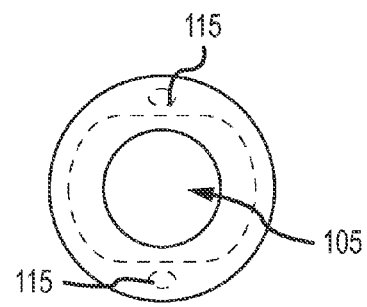
Figure 8C:
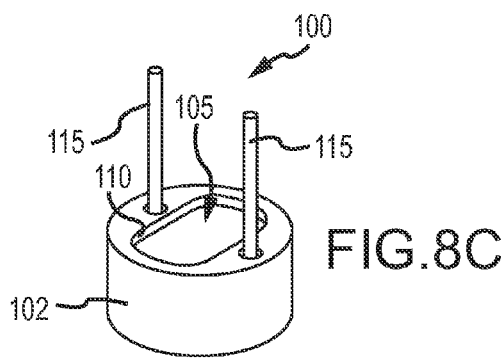

As can be understood from FIGS. 8A-8G, in one embodiment, the delivery device 15 includes a delivery catheter or sheath 20, a cutting mechanism 45 that includes an independent cutting strip, knife or blade that is controlled by separate wires and a guide track 100. As shown in FIGS. 8A-8C, the guide track 100 includes a base 102 and at least one anchor post 115, and further defines a plurality of lumens including a coil lumen 105 and at least one cutting mechanism lumen or slot 110. The coil lumen 105 is configured to receive the coil 10 and provides an exit path 125 for the coil 10 from the proximal end through the distal end of the catheter 20. The anchor post 115 is configured to anchor the guide track 100 in the catheter 20.

Figure 8D:
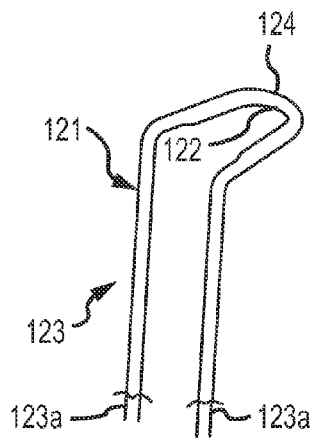
Figure 8E:
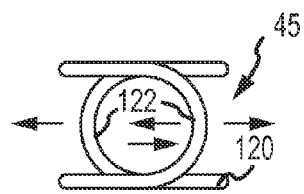
Figure 8F:
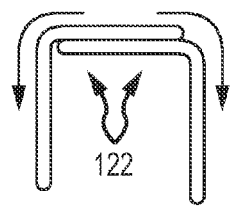
Figure 8G:
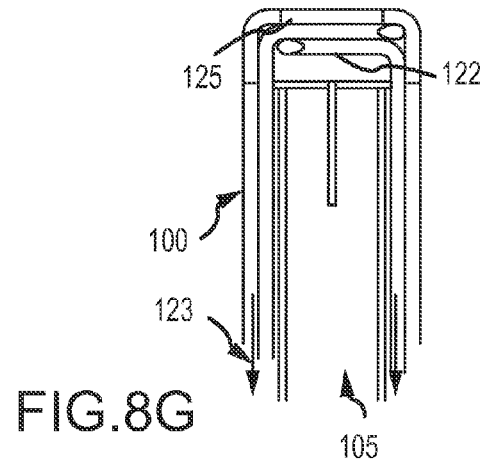

The cutting mechanism lumen or slot 110 receives a cutting mechanism 45 such as a cutting strip, knife, or blade. As illustrated in FIGS. 8D-8F, in one embodiment, the cutting mechanism is a double blade 120. The double blade 120 is formed from a wire 123, such as nitinol or stainless steel. As indicated in FIG. 8D, the wire 123 transitions from a round wire 121 into a flattened wire 124 around a 180° radius and is sharpened on an inner diameter to create a cutting edge 122. As shown in FIG. 8E, the double blade 120, in a coil deployment state, defines an opening through which the coil 10 can pass. As can be understood from FIGS. 8E and 8G, and with reference to FIG. 8F, when it is desired to cut the coil 10, the surgeon can engage the proximal ends 123a of the wire 123, thereby pulling the cutting edges 122 of the blades 120 together into a cutting or engagement state, as indicated in FIG. 8E, to cut the coil 10.

In use, the occlusion device or continuous embolic coil 10 is loaded into a first tubular delivery body 20 in a non-expanded (or pre-deployed or storage) state, e.g., via the needle tube/hub introducer 37 coupled thereto and that is configured to receive the coil 10 from, for example, the coil dispenser 35. Once the surgeon has placed the first tubular delivery body 20 into the proper location, the occlusion device or continuous embolic coil 10 may be advanced by an advance/retract mechanism 25, such as actuation feature 40, out of the delivery body 20. The straightened continuous coil 10 (in non-expanded shape) is deployed by advancing it down the delivery body 20, using an advance/retract mechanism 25, such as actuation feature 40, to deliver it out the distal end of the first tubular delivery body 20 at the target occlusion site 30. Once the surgeon determines that a desired amount of coil 10 has been delivered to the target site, the surgeon can engage the proximal ends 123a of the wire 123, thereby pulling the cutting edges 122 of the blades 120 together, as indicated in FIG. 8E, to cut the coil 10. After the coil is cut, the cutting mechanism 45 is disengaged from the coil 10 by releasing the proximal ends 123a of the wire 123 thereby transitioning the double blades 120 back into a coil deployment state. The surgeon can continue to deploy the coil 10 into the target occlusion site unobstructed by the cutting mechanism 45 as desired.

As can be understood from FIG. 9, the cutting mechanism 45 may be positioned at a proximal end of the first tubular delivery body 20. Such a location may be used when the resulting delivery length is not critical to the application. A simpler mechanism can be used that would cut the coil at the proximal end, allowing the physician to simply push the cut end through the delivery catheter with either the additional coil or a separate instrument such as a guidewire. This allows for continued use of current delivery catheters (a first tubular delivery body) without modification to incorporate a cutting mechanism at the distal end. In one such embodiment, the delivery device 15 includes a coil dispenser 35 coupled to a first tubular delivery body, such as a delivery catheter or sheath 20 via a catheter/sheath hub 23. The device 15 may include an actuation mechanism 40, such as a thumb wheel, to advance and retract the coil 10. A cutting mechanism 45 such as a blade is positioned in or on the hub 23. The cutting mechanism 45 may be coupled to an actuator button or knob 100 having a safety mechanism 102, such as a pre-cut release to prevent the blade from engaging or cutting the coil 10 before actuation by the surgeon. The safety mechanism 102 may be a knob, tab or button that is rotated or pushed before the cutting mechanism 45 can be actuated.

In use, the coil occlusion device 10 is loaded into the first tubular delivery body 20 of the delivery device 15 in a non-expanded (or pre-deployed or storage) state, e.g., via the needle tube/hub introducer 37 coupled thereto and that is configured to receive the coil 10 from, for example, the coil dispenser 35. Once the surgeon has placed the first tubular delivery body 20 into the proper location, the coil device 10 may be advanced by an advance/retract mechanism 25, such as actuation feature 40, out of the delivery body 20. The straightened continuous coil 10 (in a non-expanded state) is deployed by advancing it down the first tubular delivery body 20, using a an advance/retract mechanism 25, such as actuation feature 40, to deliver it out the distal end of the first tubular delivery body 20 at the target occlusion site 30. Once the surgeon determines that a desired amount of coil 10 has been delivered to the target site, the surgeon can unlock, release or rotate the safety mechanism 102 (as appropriate), engage (press down on) the actuator button 100 to depress the blade 45 into the coil 10 and cut the coil 10 at the proximal hub 23. Once the coil has been cut, the surgeon can release the actuator button 100, thereby releasing the blade 45 from the coil 10 and the blade 45 and button 100 return to their locked position, thereby allowing unrestrained continued coil 10 delivery as desired.

As can be understood from the previous discussion, the "cut to length" feature 45 is at least partially enabled by the described radiopaque polymer coil technology. A clear, non-radiopaque polymer material would not be visible under fluoroscopy or x-ray and subsequently, a physician would not be able to discern the location/position of the coil in order to determine when/where to trim its length. A metal coil would represent significant challenges in designing a robust cutting mechanism to assure the ends of the coil were clearly cut without entanglement that could cause potential patient harm if not severed completely. Likewise, delivery of continuous metal coil would present some significant challenges to assure that a sharp edge is not left on the coil that might subsequently cause tissue trauma or damage to the vessel by either end of the cut coil. Finally, a polymer coil with an internal reinforcing strand wherein both are cut to separate the coil assures that no particulate or coil fragments will be generated during the cutting or segmenting of the coil in situ which could cause risk of an unintended embolus.

Figure 10:
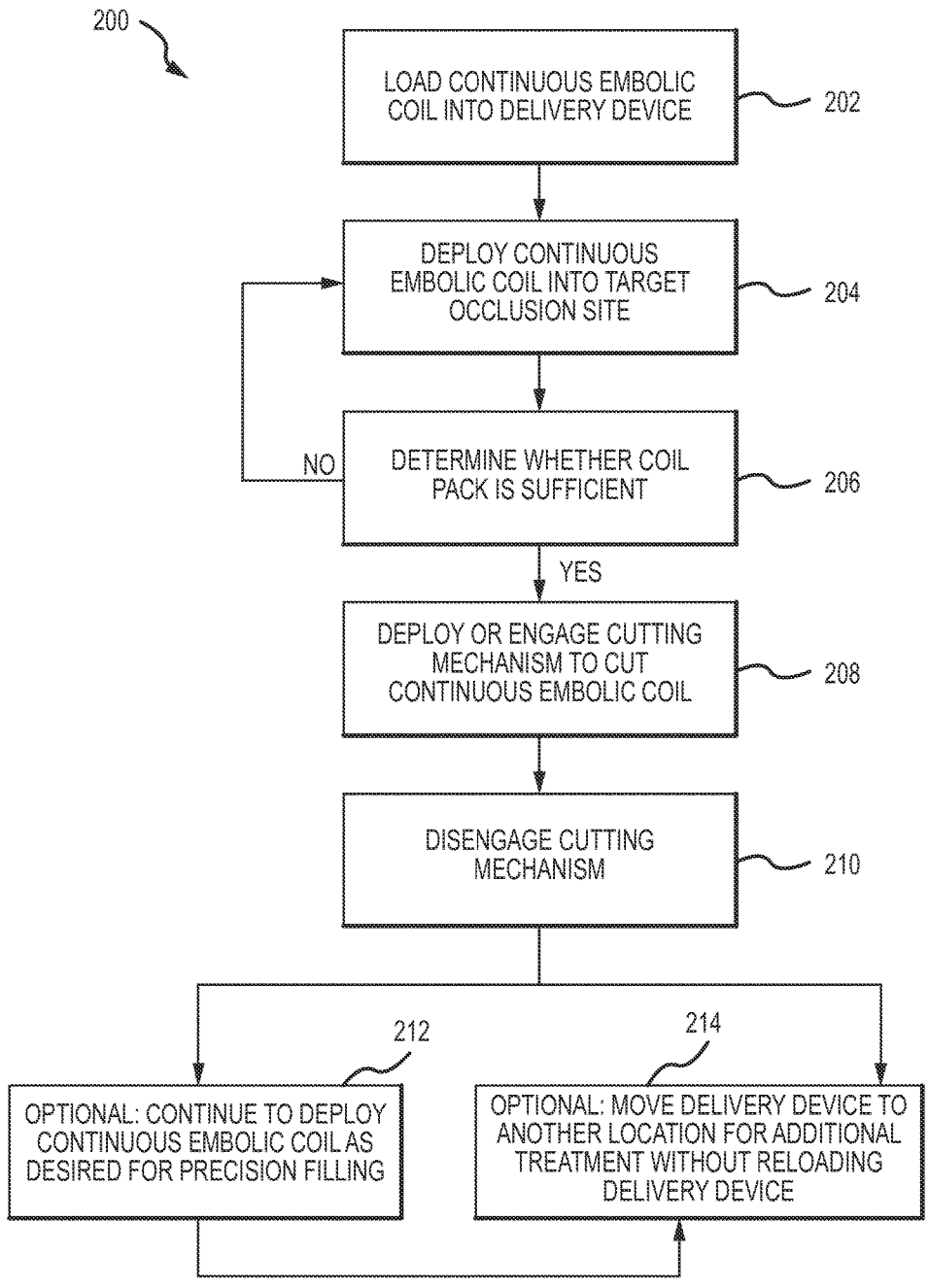
FIG. 10 is a flow diagram of an exemplary method of using an embodiment of the occlusion system in accordance with the aspects of the present disclosure.

FIG. 10 illustrates one embodiment of a method of using a delivery device configured to deliver a single continuous embolic coil. In use, and in accordance with the exemplary method 200, in operation 202, the occlusion device or continuous embolic coil 10 (e.g., the single continuous embolic coil) is loaded into a first tubular delivery body 20, such as a catheter, extending from the delivery body 20 in a non-expanded (or pre-deployed or storage) state. It can be appreciated that in some embodiments, there may also be a second tubular delivery body that is utilized with the first tubular delivery body as disclosed elsewhere herein. Once the surgeon has placed the first tubular delivery body 15 into the proper location, and in accordance with operation 204, the coil device 10 may be advanced by an advance/retract mechanism 25, such as an actuation mechanism 40, out of the tubular body 20. The straightened coil member 10 (in a non-expanded state) is deployed by advancing the coil 10 down the first tubular delivery body 20, using an advance/retract mechanism 25, such as an actuation feature 40, to deliver it out the distal end of the delivery body 20 at the target occlusion site 30. In operation 204, the surgeon then determines whether the coil pack is sufficient. In one embodiment, this determination is made by monitoring the position of the coil occlusion device 10 on a fluoroscope monitor or other clinical medical imaging system in which the coil 10 may be seen. If the coil pack is not sufficient, then the surgeon can continue to deploy the coil 10 (back to operation 204). If the coil pack is sufficient, and in accordance with operation 208, the surgeon can deploy or actuate a cutting mechanism 45, such as a cutting mechanism described herein, to cut the coil occlusion device 10. The cutting mechanism 45 may be positioned at a distal end of the first tubular delivery body 20 or at a proximal end of the first tubular delivery body 20. In accordance with operation 210, once cut, the surgeon can disengage the cutting mechanism 45 from the coil occlusion device 10. Optionally, and in accordance with operation 212, the surgeon may continue to deploy the coil 10 into the first occlusion site as desired for precision filling. Optionally, and in accordance with operation 214, the surgeon may move the delivery device 15 (or a portion thereof) to another target occlusion site for additional treatment without reloading the device 15.

It should be appreciated that while the method 200 refers to delivery of the coil 10 through the first tubular delivery body 20, such as catheter 20, in accordance with some embodiments described herein, a second tubular delivery body 55, such as a cannula 55, may be coaxial with or otherwise positioned in the first tubular delivery body 20. Accordingly, in some embodiments of the method 200, coil 10 may be deployed through both the first tubular delivery body 20, such as catheter 20, and the second tubular delivery body 55, such as cannula 55. It should be appreciated that the operations of the method 200 may be performed in the order illustrated, in another suitable order and/or one or more operations may be performed simultaneously. Moreover, in some embodiments, the method 200 may include more or fewer operations than those illustrated.

Thus, as can be understood from the discussion found herein, the delivery device and its various configurations as disclosed herein address current key clinical deficiencies that are unmet with existing delivery devices for multiple short or discrete polymer coils and with other vascular occlusion devices, such as metal mesh plugs, and the associated challenges discussed herein.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter may be used interchangeably for purposes of this description. The exemplary drawings are for purposes of illustration only and the dimensions, positions, order and relative sizes reflected in the drawings attached hereto may vary.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An occlusion system for occluding a target vessel or filling an aneurysmal space comprising
   a continuous embolic coil;
   a delivery device comprising a first end and a second end;
   a first tubular delivery body having a proximal end and a distal end, and comprising the second end of the delivery device, wherein
      the first tubular delivery body defines a lumen through which the continuous embolic coil is deployable from an axial opening in the distal end into a target vessel to be occluded or aneurysmal space to be filled; and
      the first end of the delivery device is configured to couple with a needle tube/hub introducer through which the first tubular delivery body accesses a vessel;
   a cutting mechanism positioned in or coupled to the distal end of the first tubular delivery body, wherein the cutting mechanism comprises a garrote configured to cut the continuous embolic coil perpendicular to both a longitudinal axis of the first tubular delivery body and a longitudinal axis of the embolic coil once a desired first length of the continuous embolic coil is deployed; and
   a cutting actuation mechanism mounted on the delivery device proximal to the first tubular deliver body and operably coupled with the garrote, wherein
   the garrote comprises two wires forming respective opposing cutting sections at the distal end of the first tubular body and at least one end of each wire extends axially along a length of the first tubular delivery body and is operably connected to the cutting actuation mechanism.

2. The occlusion system of claim 1, wherein the first end of the delivery device further comprises a coil dispenser coupled to the needle tube/hub introducer, wherein the coil dispenser stores the single continuous embolic coil therein.

3. The occlusion system of claim 2, wherein the coil dispenser further comprises a coil shaped channel around which the continuous embolic coil is wound and held within the coil dispenser until deployment.

4. The occlusion system of claim 1 further comprising an actuation mechanism to advance and/or retract the continuous embolic coil through the delivery device.

5. The occlusion system of claim 4, wherein the actuation mechanism is a thumb wheel or a friction wheel.

6. The occlusion system of claim 1 further comprising
a second tubular delivery body having a distal end and a proximal end; and
a cutting actuation mechanism mounted on the delivery device proximal to the first tubular delivery body and operably coupled with the garrote; wherein
the garrote is coupled to or integral with the distal end of the second tubular delivery body;
a void space is defined within and along a length of the first tubular delivery body between the continuous embolic coil and an inner wall of the first tubular delivery body; and
the second tubular delivery body is positioned within the void space adjacent to or about the continuous embolic coil.

\* \* \* \* \*